United States Patent [19]

Broderick

[11] Patent Number: 4,883,057

[45] Date of Patent: Nov. 28, 1989

[54] CATHODIC ELECTROCHEMICAL CURRENT ARRANGEMENT WITH TELEMETRIC APPLICATION

[75] Inventor: Patricia A. Broderick, Bronx, N.Y.

[73] Assignee: Research Foundation, The City University of New York, New York, N.Y.

[21] Appl. No.: 905,579

[22] Filed: Sep. 9, 1986

Related U.S. Application Data

[63] Continuation-in-part of Ser. No. 608,426, May 9, 1984, abandoned.

[51] Int. Cl.$^4$ ............................................. A61B 5/07
[52] U.S. Cl. ................................... 128/631; 128/635; 128/904
[58] Field of Search ............... 128/631, 635, 731, 734, 128/904; 204/1 T, 400, 403

[56] References Cited

U.S. PATENT DOCUMENTS

| | | | |
|---|---|---|---|
| 3,850,161 | 11/1974 | Liss | 128/731 |
| 3,868,578 | 2/1975 | Oldham | 328/128 X |
| 3,872,252 | 3/1975 | Malchman et al. | 128/904 X |
| 4,319,241 | 3/1982 | Mount | 128/904 X |
| 4,424,812 | 1/1984 | Lesnick | 128/419 PG |
| 4,499,552 | 2/1985 | Kanazawa | 364/802 |

OTHER PUBLICATIONS

Lindsay et al., "Microcomputer . . . Electrochemistry", Chem. Biomed. and Environ. Instrumentation, 10(3), 311–330 (1980).
K. Oldham, "Semi . . . Implementation", Anal. Chem., vol. 45, No. 1, pp. 39–47 (1973).
Kissinger et al., "Voltametry . . . Measurement", Brain Research, vol. 55, pp. 209–213 (1973).
Clemens et al., "Changes . . . Rats", Brain Research, vol. 267, pp. 183–186 (1983).

Primary Examiner—Nam X. Nguyen
Attorney, Agent, or Firm—Morgan & Finnegan

[57] ABSTRACT

This invention relates to a method for producing a cathodic, or reduction, current used in an in vivo semidifferential, semiderivative and/or semiintegral electrochemical method for achieving routine, reliable, and reproducible measurements of the dynamics of neurochemicals and neurochemical-like materials for the purpose of medical diagnosis in the body and brain of animals and in human patients. The method of this invention also permits the detection of biological markers to delineate diseased states for purposes of preventative and therapeutic medicine. Telemetric applications and automated devices for diagnostic and monitoring purposes are also described.

34 Claims, 22 Drawing Sheets

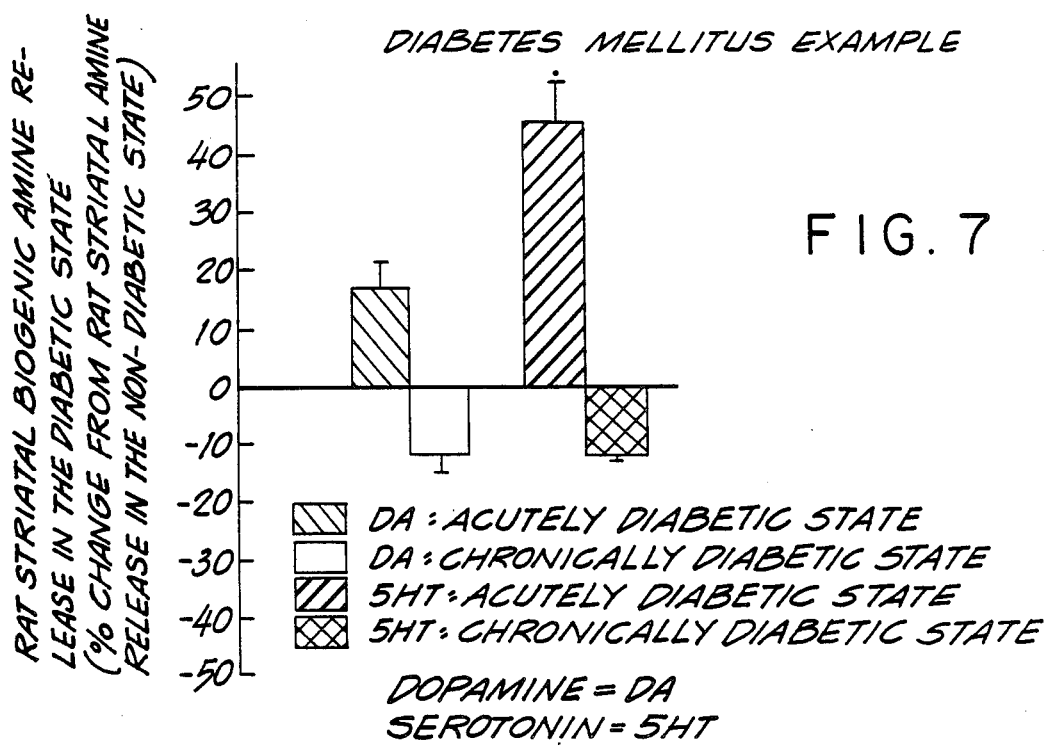
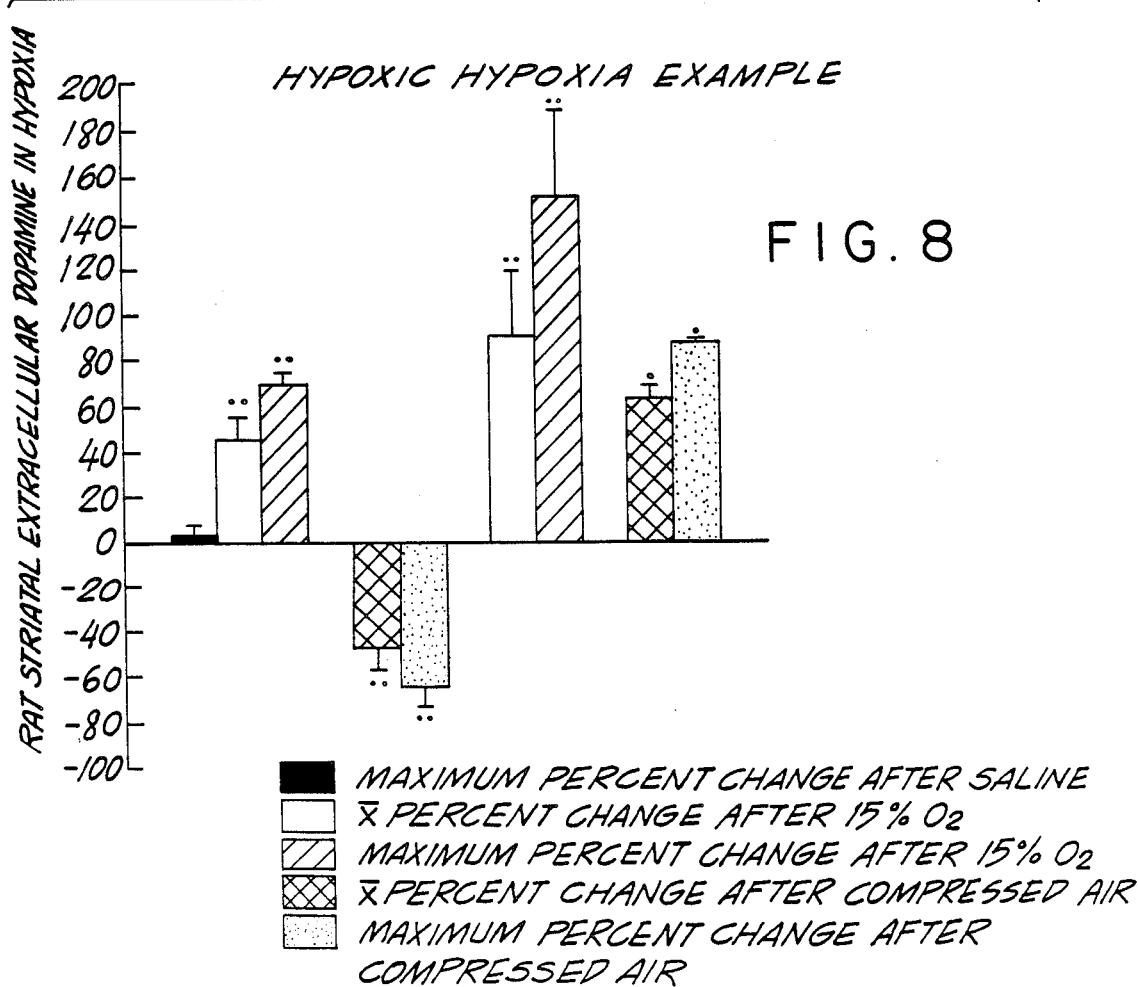

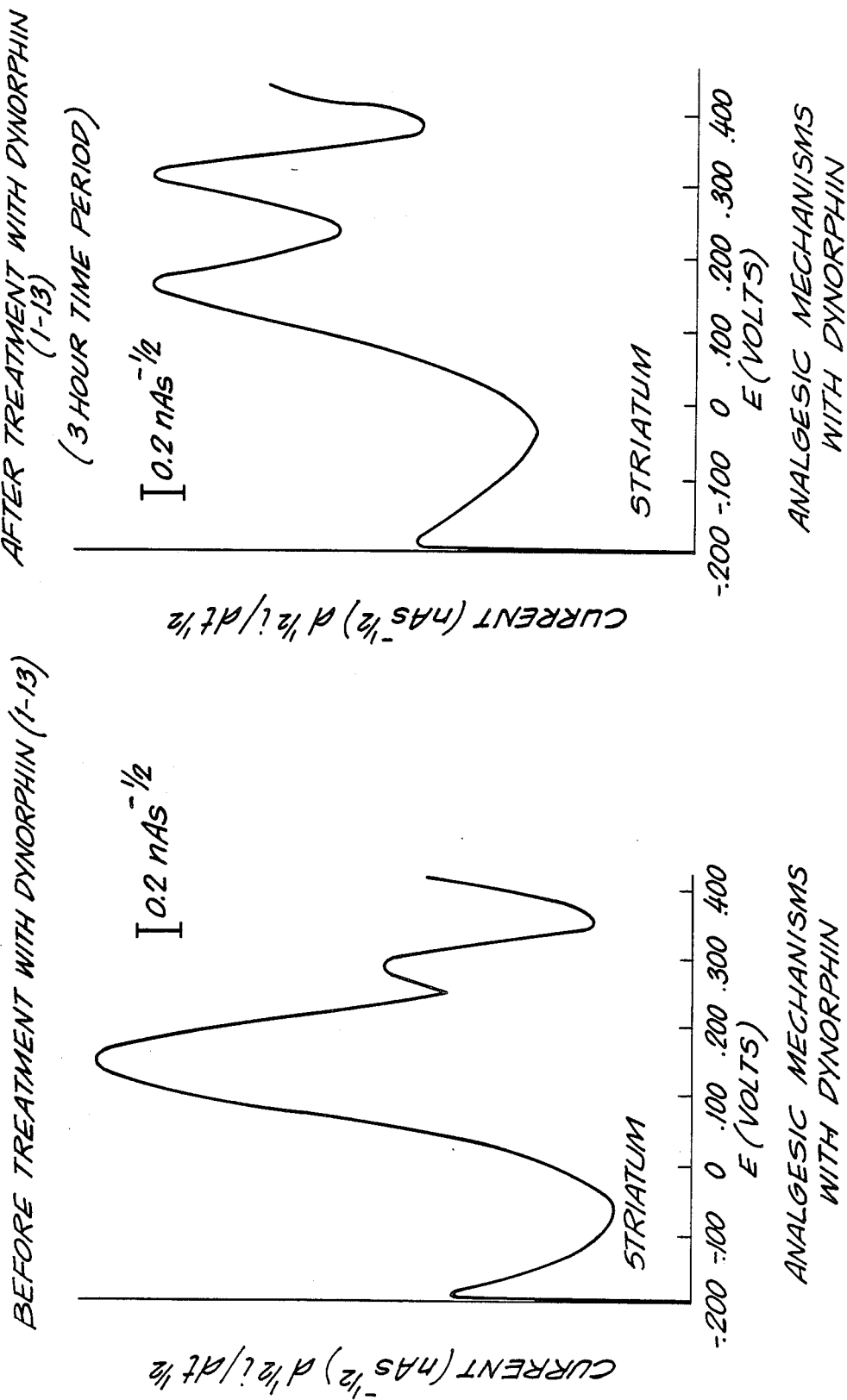

POST-MORTEM DOPAMINE RELEASE

WHERE +0.08V REPRESENTS THE OXIDIZED SPECIES OF 6OHDA AND -0.32V REPRESENTS THE REDUCED SPECIES OF 6OHQ.

DIRECT COUPLING AMPLIFIER
WITH TWO TRIODES

METHOD FOR CHANNEL O

1.     C H R O M A T O C H A R T  V1.07
2. RUN IDENTIFICATION/FILES OPTIONS
3. TITLE $ AUTO
4. DATE $ 9/25/85
5. TIME $ AM
6. OPERATOR$
7. CONDITIONS$           V
8. DISK FILENAME.S,D $ AUTO, S6, D2
9. SAVE DAT.FILE (Y:N) $ Y
10. SAVE BAS.FILE (Y:N) $ Y
11. SAVE PEK.FILE (Y:N) $ Y
12. GRADIENT FILENAME.S,D$
13. STANDARD FILENAME, S,D$_____
14.
15. DATA ACQUISITION OPTIONS
16. ADALAB SLOT (0:7) : 2
17. RAM SLOT    (0:7) : 0
18. RAM ADDRESS, K (1:255): 1
19. RUN LENGTH, K  (1:64): 1
20. FIRST RUN # (1:127): 13
21. # REPEAT RUNS (0:127): 0
22. AVERAGE # POINTS (1:8) # 4
23. SUM # POINTS     (1:8) : 2
24. CHART DELAY     (1:127) : 10
25. CHART WIDTH. 100'S (1:4) : 4
26. CHART Y SCALE    (1:255) : 20
27. CHART OFFSET (-9999:9999) : -10
28. CHART HARDCOPY (Y:N) $ Y
29.
30. INTEGRATION/REPORT OPTIONS
31. SMOOTHING WIDTH (3:15) : 9
32. INIT. SLOPE THRESH. (1:32767) : 10000
33. MINIMUM BASELINE WIDTH (1:99) : 70
34. INITIAL PEAK WIDTH (1:99) : 10
35. WIDTH % CHANGE   (1:100) : 70
36. SHOULDER % WIDTH (1:100) : 100
37. MIN. PEAK AREA (1:32767) : 100
38. REVIEW BASELINE (Y:N) $ N
39. TIME UNITS IN REPORT (SEC:MIN) $ SEC
40. REPORT PRINTER SLOT #(0:7) : 1
41. CHART HARDCOPY (Y:N) $ Y
42. CHART WIDTH, 100'S (1:4) : 2
43. CHART X SCALE    (1:20) : 1
44. CHART Y SCALE  (-255:255) : 20
45. CHART OFFSET (-9999:9999) : -10

FIG. 28(a)
SH. 1 OF 2

EVENT CONTROL SCHEDULE

| EVT | SECONDS | TYPE | BIT | ON/OFF | GOTO |
|-----|---------|--------|-----|--------|------|
| 1 | 0 | STATUS | 1 | | |
| 2 | 1 | SWITCH | 2 | OFF | |
| 3 | 121 | SWITCH | 1 | OFF | |
| 4 | 136 | STATUS | 5 | | |
| 5 | 185 | STATUS | 1 | | |
| 6 | 242 | SWITCH | 1 | ON | |
| 7 | 243 | SWITCH | 2 | ON | |
| 8 | 244 | SWITCH | 3 | OFF | |
| 9 | 245 | SWITCH | 3 | ON | |
| 10 | 400 | STATUS | 1 | | |
| 11 | 401 | STATUS | 0 | | |

FIG. 28(a)
SH. 2 OF 2

METHOD FOR CHANNEL 0

1. C H R O M A T O C H A R T V1.07
2. RUN IDENTIFICATION/FILES OPTIONS
3. TITLE$ VIVO
4. DATE$ 4/8/86
5. TIME$ AM
6. OPERATOR $
7. CONDITIONS$           V
8. DISK FILENAME,S,D$ VIVO,S6,D2
9. SAVE DAT.FILE   (Y:N) $ Y
10. SAVE BAS.FILE  (Y:N) $ Y
11. SAVE PEK. FILE (Y:N) $ Y
12. GRADIENT FILENAME,S,D $
13. STANDARD FILENAME,S,D $_____
14.
15. DATA ACQUISITION OPTIONS
16. ADALAB SLOT (0:7) : 2
17. RAM SLOT          (0:7) : 0
18. RAM ADDRESS,  K(1:255) : 1
19. RUN LENGTH ,  K  (1:64) : 1
20. FIRST RUN #         (1:127) : 1
21. # REPEAT RUNS    (0:127) : 0
22. AVERAGE # POINTS (1:8) # 4
23. SUM # POINTS       (1:8) : 2
24. CHART DELAY        (1:127) : 10
25. CHART WIDTH, 100'S  (1:4) :  4
26. CHART Y SCALE     (1:255) : 20
27. CHART OFFSET (-9999:9999) : -10
28. CHART HARDCOPY (Y:N)$ Y
29.

FIG. 28(b)
SH. 1 OF 2

30. INTEGRATION/ REPORT OPTIONS
31. SMOOTHING WIDTH (3:15) : 5
32. INIT. SLOPE THRESH. (1:32767) : 500
33. MINIMUM BASELINE WIDTH (1:99) : 1
34. INITIAL PEAK WIDTH (1:99) : 80
35. WIDTH % CHANGE     (1:100) : 70
36. SHOULDER % WIDTH (1:100) : 80
37. MIN. PEAK AREA (1:32767) : 100
38. REVIEW BASELINE (Y:N)$ N
39. TIME UNITS IN REPORT (SEC:MIN) $ SEC
40. REPORT PRINTER SLOT #(0:7) : 1
41. CHART HARDCOPY (Y:N)$ Y
42. CHART WIDTH, 100'S    (1:4) : 2
43. CHART X SCALE       (1:20) : 1
44. CHART Y SCALE  (-255:255) : 20
45. CHART OFFSET (-9999:9999) : -10

EVENT CONTROL SCHEDULE

| EVT | SECONDS | TYPE | BIT | ON/OFF | GOTO |
|---|---|---|---|---|---|
| 1 | 0 | STATUS | 1 | | |
| 2 | 1 | SWITCH | 2 | OFF | |
| 3 | 121 | SWITCH | 1 | OFF | |
| 4 | 136 | STATUS | 5 | | |
| 5 | 185 | STATUS | 1 | | |
| 6 | 242 | SWITCH | 1 | ON | |
| 7 | 243 | SWITCH | 2 | ON | |
| 8 | 244 | SWITCH | 3 | OFF | |
| 9 | 245 | SWITCH | 3 | ON | |
| 10 | 400 | STATUS | 1 | | |
| 11 | 401 | STATUS | 0 | | |

FIG. 28(b)
SH. 2 OF 2

THE BASIC OPERATIONAL AMPLIFIER CIRCUIT
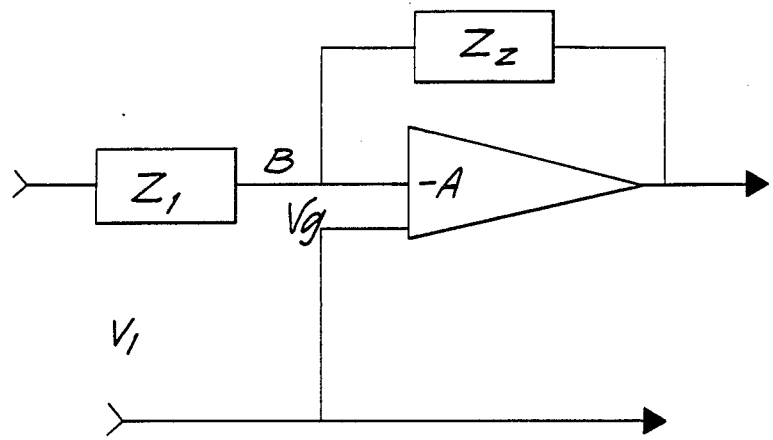
GENERALIZED OPERATIONAL AMPLIFIER CIRCUIT.
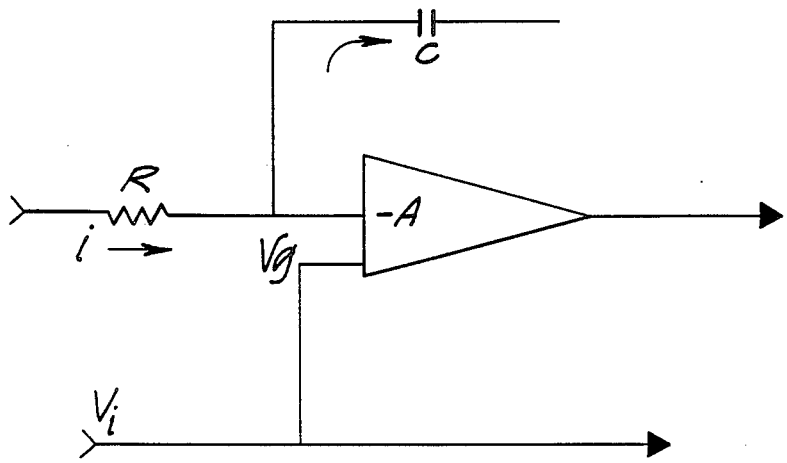
AN OPERATIONAL AMPLIFIER INTEGRATOR
FIG. 29
(PRIOR ART)

CATHODIC ELECTROCHEMICAL CURRENT ARRANGEMENT WITH TELEMETRIC APPLICATION

This application is a continuation-in-part of U.S. patent application Ser. No. 608,426, filed May 9, 1984, which is incorporated herein by reference.

BACKGROUND OF THE INVENTION

This invention relates to the use of an in vivo electrochemical method to measure the amounts of biogenic chemicals present in the body and brain of an animal or a human being. More particularly, it relates to the use of in vivo semiderivative voltammetric measurements of biogenic chemicals, particularly neurotransmitters, such as amines, amine metabolites, ascorbic acid, amino acids and neuropeptides produced in reaction to psychopharmacological agents and neuropsychopharmacological agents such as analgesics, antipsychotic drugs, anti-depressants, and other modulators of brain and peripheral neurochemistry in diseased and healthy states.

It has been known to those possessing ordinary skill in the art that it is possible to measure certain limited types chemicals using in vivo electrochemistry in the brains and suborgans of nonhuman primates and other animals. This measurement has been accomplished using such facets of electrochemical measurements as chronoamperometry, differential pulse voltammetry, double differential pulse voltammetry, linear scan voltammetry, and semiderivative voltammetry. In all of these methods, a working electrode, a reference electrode and an auxiliary electrode are attached to the brain or other organ of the animal to be studied. A controlled potential is applied to the working electrode and the current passing between the working electrode and the reference electrode is monitored as a signal and used to measure basal neurotransmitter release and any alterations in brain neurochemistry. The signal is directly related to the chemical concentration of the neurotransmitter released from the neuronal brain membrane presynaptically, or possibly postsynaptically and represents an instantaneous readout of rate of neuronal mechanism. The signal may also be related to inhibition of normal reuptake of neurotransmitter at the neuronal membrane and may be a summation of release and reuptake processes, especially during treatment. The prior art teaches that this current is an anodic (oxidation) current, based on scientific principle. This signal is recorded as a graph indicating change in current with respect to time (chronoamperogram) or voltage (voltammogram).

It is known that voltammetric measurements can be used to detect certain biogenic substances in the brain of rats [Kissinger, P. T.; Hart, J. B.; Adams, R. N.; "Voltammetry in Brain Tissue - A New Neurophysiological Measurement", *Brain Research*, 55 (1973), p. 209.]. Other researchers have also detected signals in the brains of living rats, as follows: McCreery, et al., Brain Res. Vol. 73 (1974), p. 23; Gonon, et al, Brain Res. Vol. 223 (1981), p. 69; Lane, et al., J. Electroanal. Chem., Vol. 95 (1979), p. 117; Clemens and Phebus, Brain Res., Vol. 267 (1983), p. 183 and Millar, et al., Eur. Pharmacol. Vol. 109 (1985), p. 341.

There has been, however, little or no description of circuitry for in vivo electrochemical circuits even though certain improvements have been made in voltammetric measurements since the linear scan for in vivo electrochemistry method was first described for measuring biogenic chemicals. One such improvement was the in vitro processing of the linear scan current signal as the first half-derivative of the linear signal [Oldham, "Analytical Chemistry" Vol. 45 (1973) p. 39 and U.S. Pat. No. 3,868,578; Kanazawa, U.S. Pat. No. 4,449,552]. However, neither Oldham nor Kanazawa describe circuitry applicable for detection of organic materials in living organisms. Although they describe oxidation and reduction reaction species, they do not describe cathodic (reduction) currents. For the purposes of this application, cathodic current is defined as current based on the acquisition of electrons by neurochemicals within the organ or suborgan and flowing away from an indicator electrode situated within the organ or suborgan. Anodic current is defined as current based on the loss of electrons by neurochemicals in the organ or suborgan and flowing toward an indicator electrode situated within the organ or suborgan.

When applied to the brain, or other body organs, this type of processing should result in a semidifferentiated voltammogram having sharper peaks, which then allows greater separation between peaks representing chemical substances and which are easier to read than previous, linear voltammograms. Older conventional methods did not allow individual detection of amines because similar electrochemical potentials, accompanying many of the biogenic amines and other chemicals, are set by the catechol moiety and not by the alkyl moiety of the biogenic amine and thus did not allow for separation of peaks between different amines, all of which contain the catechol moiety. Semiderivation or semidifferentiation of the signal briefly allowed somewhat better detection. Many practitioners, however, have found it difficult or impossible to obtain reproducible measurements routinely using what is known as the in vivo electrochemistry technique of semiderivative or semidifferential voltammetry.

Although telemetric devices have been produced in the past, as described in U.S. Pat. No. 4,424,812 (Lesnick) and U.S. Pat. No. 3,882,277 (DePedro), telemetric devices for monitoring brain signals have not been described. Neither of these patents describe monitoring signals produced electrochemically either in vivo, in vitro or in situ.

The wisdom of the prior art indicates that an oxidation current, or anodic current, should be used to detect biochemical species in the brain. Previous researchers assumed that in living systems, all chemical species which could be detected by electrochemical signals were converted into stable oxidized species. Most of the previous researchers also assumed that all biogenic chemical reactions produced oxidized species without producing stable reduced species. These assumptions have provided only a limited tool for diagnosing the mental and physiological states of living organisms, as only a limited number of biogenic chemicals can be detected using prior art methods.

Accordingly, it is an object of this invention to provide a method for measuring biogenic chemicals.

It is a further object of this invention to provide an in vivo electrochemical method for measuring biogenic chemicals.

It is still a further object to provide a useful way to measure biogenic chemicals using the semiderivative or semidifferential voltammetric technique to produce a cathodic current.

It is a further object of this invention to provide the circuitry for such a cathodic current.

It is still a further object of this invention to provide a cyclic voltammogram within the context of the cathodic current.

It is a further object of this invention to provide an in vivo electrochemical method for measuring biogenic amines, amine metabolites, ascorbic acid, amino acids and neuropeptides and other neurotransmitters and modulators of brain neurochemistry.

It is still a further object of this invention to provide an in vivo electrochemical method for measuring alterations in biogenic brain chemicals in relation to the administration, both peripheral and central, of psychopharmacological agents and neuropsychopharmacological agents such antidepressants, analgesics, antianxiety agents, anti-panic agents, anti-manic/depressive agents, calcium blocking agents, agents of addiction, other neuropeptides, enkephalinamides, dynorphin and other potential modulators of brain neurochemistry.

It is another object to provide an in vivo electrochemical method for interpreting these alterations in brain neurochemistry in light of diagnosing mental illness, Alzheimer's disease, and other diseased states, vis-a-vis healthy states, and developing new and more effective psychotherapeutic agents and other clinical applications.

It is a further object of this invention to provide an in vivo electrochemical method for measuring the levels and dynamic changes of biogenic chemicals with an instantaneous readout of rate in humans, in vivo.

It is still a further object of this invention to provide a means for studying the dynamic levels and/or release of biogenic chemicals produced during certain behavioral manifestations and thus provide a method for determining the causes of these manifestations.

It is another object of this invention to provide a method by which to correlate the production of certain biogenic chemicals with electrophysiological measurements.

Another object of this invention is the development of electrodes which are extremely selective to biogenic chemicals, which could be and are biological markers, and to describe the modification of such by biological brain and body fluids.

It is still a further object of this invention to provide a detailed description of reference, indicator (working) and auxiliary electrodes for the purpose of teaching the art of electrode fabrication.

An additional object of this invention is to provide a means for diagnosing illness in vivo, as opposed to the current manner of diagnosing illness from markers, i.e. post-mortem, from frozen brains and body organs.

Another object of this invention is to provide a telemetric method of diagnosing dynamic release mechanisms of biogenic chemicals such that a human patient may be continuously monitored without the impediment of wires.

Still another object of this invention is to describe peaks representing biogenic chemicals and neurotransmitters which have heretofore not been described and which influence behavior.

Still a further object of this invention is to provide a means for automating the in vivo monitoring of an animal or patient.

Yet another object of this invention is to provide neurochemical profiles from different brain regions, providing a neurochemical mapping device for diagnosis.

SUMMARY OF THE INVENTION

Unexpectedly, the inventor has found that a vast number of biochemical reactions produce a large number of biogenic chemical species heretofore unknown and undetectable. Using the method of this invention, it has now been found that semiderivative (semidifferential) voltammetry can be used for measuring concentrations and an instantaneous readout of rates of release and/or reuptake of biogenic chemicals in vivo in a reliable and repeatable manner according to the method of this invention. More particularly, it has been found, also unexpectedly, that the current produced by biogenic chemicals when monitored by a semiderivative electrochemistry device is only measurable by circuitry which provides a cathodic current. Thus, the method of this invention relates to the measurement of a current produced in the body of an animal or a human being, the signal of which is processed by a cathodic current vis-a-vis previous circuits which are anodic. This permits the measurement of stable reduced and oxidized species in vivo with a cathodic current, heretofore inconceivable.

The method of this invention is particularly well-suited to measuring biogenic chemicals in vivo, that is, in a living animal or human being, although this method can be used to measure such chemicals in vitro. It was previously thought that biochemical reactions, in vitro, and quintessentially in vivo could only be measured by anodic currents. However, using the method of this invention, one can routinely detect oxidized and reduced species, with cathodic currents, expanding the range of detection considerably for the field of diagnosis in pharmacotherapeutics and medicine.

The method of this invention describes an electronic circuit arrangement acting as an electrochemical cell to effectuate a cathodic (reduction) current in vivo, in vitro and in situ, which is faradaic in nature. The cathodic current can be derived from an electrochemical cell; the cathodic current is unknown within the current concepts of brain neurophysiology and in vivo electrochemical reactions. The cathodic current serves as a specific detector for recognizing electroactive materials (and even non-electroactive materials with the use of antibodies) for biomedical diagnosis of diseased states, vis-a-vis healthy states. Cathodic analysis and detection of reversible and irreversible reduced or oxidized compounds, directly applicable to pharmacotherapeutics in biomedical research, were heretofore precluded.

BRIEF DESCRIPTION OF DRAWINGS

FIG. 3A depicts a graph drawn according to conventional electrochemical format wherein the axis indicating anodic (oxidation) current points downward and the axis indicating positive voltage points to the left. FIGS. 3B and 3C depict semiderivative voltammetry signals drawn according to nonconventional format, wherein the axes indicating anodic (oxidation) current points upward and the axes indicating positive voltage points to the right.

FIG. 7 is a representation of the signal obtained using the method of this invention of endogenously released striatal dopamine and serotonin in acutely and chronically diabetic rats. Results are expressed as percent change from endogenously released dopamine and serotonin in the non-diabetic rat, matched for age, sex, food and weight. Bars represent the mean values derived from six to eight rats.

FIG. 8 is a representation of the signals, obtained from using the method of this invention, of rat striatal extracellular dopamine in hypoxic hypoxia using the method of this invention. Results are expressed as percent change from basal extracellular dopamine in the same animals under normal and abnormal conditions of $O_2$ (oxygen) availability. Bars represent mean values derived from six rats.

FIG. 9a represents a semidifferential voltammogram showing basal dopamine and serotonin release from rat striatum in vivo prior to treatment with dynorphin. FIG. 9b represents a semidifferential voltammogram showing dopamine and serotonin release from rat striatum in vivo after pharmacological manipulation with dynorphin (1–13) 1.5 mg./kg. administered subcutaneously. The figure uses nonconventional electrochemical notation.

FIGS. 28(a) and 28(b) are computer programs to direct a modified Bioanalytical System (BAS) brand DCV5 detector to scan for oxidation or reduction currents in vivo (Computer Program 1) and in vitro (Computer Program 2), dependent on the type of electrochemical technique used.

FIG. 29 (a) and (b) are schematic diagrams of (a) a generalized operational amplifier circuit and (b) an operational amplifier integrator.

DETAILED DESCRIPTION OF THE PREFERRED EMBODIMENTS

The method of this invention involves implanting, preferably, three electrodes in the body, preferably the brain: a reference electrode, an auxiliary electrode and a working or indicator electrode. The reference electrode provides a zero voltage point. The auxiliary electrode maintains the current, with a potential control operational amplifier, providing a sort of "ground" in so far as "drift" is eliminated, which maintains the voltage applied between the working and the reference electrode as a constant within the time limits of detection. The working or indicator electrode is used to vary the electrical potential with respect to the reference electrode.

The current signal emitted by any biological system is produced by the charge flowing, or current, between the reference and working electrodes (this flow of charge is the current). This current varies dependent on the electrochemical reactions taking place within the organ or suborgan. The signal is preferably processed with two operational amplifiers, one for the indicator, a current measurer, and one for the reference, a follower operational amplifier processing the current between the two electrodes. The semiderivative circuit is an electrochemical circuit which is added to a circuit for linear scanning. This circuit is made up of a series of ladder networks of resistors (from about 2 kilohms to about 2 megohms) and capacitors (from about $5 \times 10^4$ to $5 \times 10^{-2}$ microfarads) which process the current signal as the analog of the first one-half derivative of the raw undifferentiated signal. The resistive capacitive network that produces the semidifferentiated signal is described in detail in "Semiintegral Electroanalysis: Analog Implementation", *Analytical Chemistry*, Vol. 45, No. 1, January 1973, by Keith Oldham, which is hereby incorporated by reference.

The novel circuitry of this invention provides the production of a reduction, or cathodic, current, which allows detection of both reduced and oxidized species heretofore undetected and precluded within these detection limits.

Figure 1:
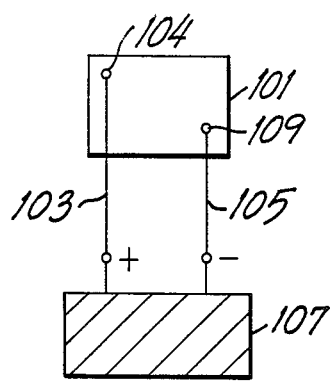
FIGS. 1 and 2 are schematic representations of two circuits which can be used in attempting to establish a semidifferential voltammetric signal.
Figure 2:
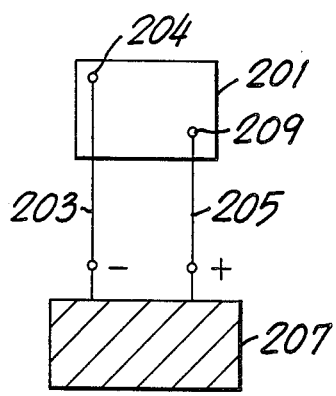

The electrodes should be situated in such a way as to accommodate a cathodic, or reduction, current from, for example, the brain. The electrodes can be situated in any specific region, such as the striatum, tuberculum olfactorium or nucleus accumbens. FIG. 1 shows a very simplified schematic view of the circuitry as it should appear in accordance with the method of this invention. The semiderivative circuit, 107, is connected to the brain, 101, via two leads: the brain lead, 103, attached to the working electrode, 104, and the reference lead, 105, which is attached to the reference electrode, 109. The current being emitted from the brain is a cathodic current, positive for reduction. Thus, in order to obtain a reliable measurement, the positive terminal of the voltammetry control should receive the emitted current signal from the brain lead which is attached to the working electrode. No signal would be produced if the leads were connected as shown in FIG. 2, which is the circuit configuration which would conventionally be expected to measure current generated by biogenic brain species. In FIG. 2, the working electrode 204 is shown implanted in the brain, 201. The brain lead, 203, is connected to the working electrode and the negative terminal of the semiderivative voltammeter, 207. This system, which produces anodic current, does not generate a recognizable signal. Ultimately, a cathodic current must be produced.

Conceptually, the indicator electrode of this invention is an inert surface which serves as an electron source or sink. The indicator electrode can be placed in specific parts of an organism or suborganism for diagnosis of diseases which range from mental and neurological problems to aging processes and malignant cervical cancers and other types of cancers, for example. As the potential is applied, the electrons from molecules or molecules of biogenic chemicals near the electrode surface can either gain electrons from the body, or source (cathodic reduction) or lose them to the indicator electrode sink (anodic oxidation). The current is dependent on the number of molecules which undergo electron transfer at the electrode surface; this is an accurate indication of the increase of species concentration in solution, in addition to an accurate assessment of the rate at which electricity is moved across the electrode and converted into charge. An instantaneous readout of rate is a unique feature of electrochemistry; this reflects in vivo release mechanisms.

Figure 11:
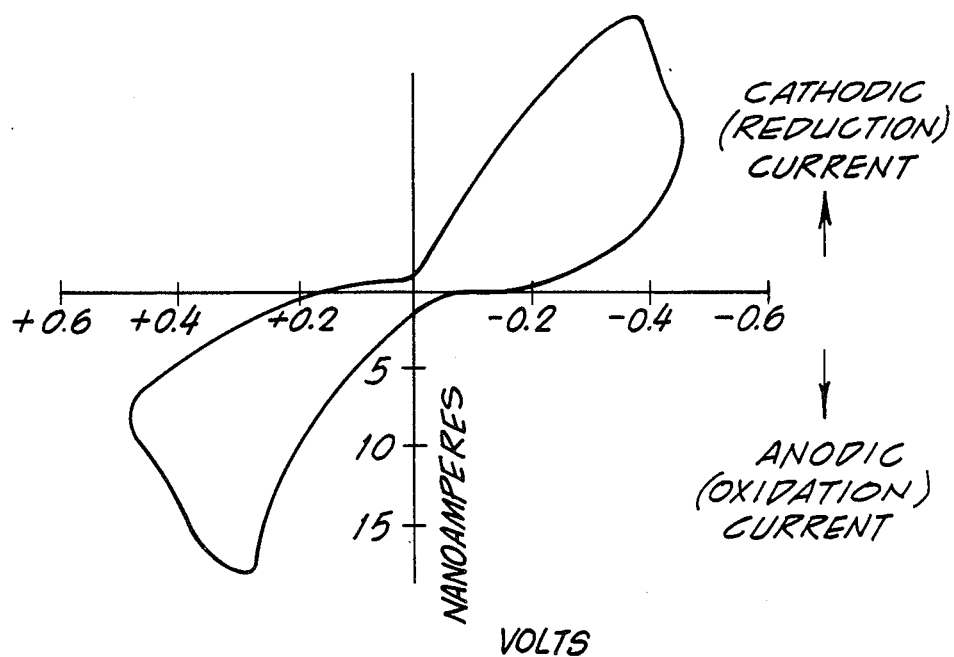
FIG. 11 is a representation of a typical linear scan cyclic voltammogram for a reversible redox reaction by electrochemical convention.

For the purposes of illustration, parts of FIGS. 3, 11 and ff and the following are provided to delineate the conventional means for interpreting electrochemical measurements with the use of drawings according to electrochemical convention. By conventional electrochemical notation, oxidation (anodic) currents are plotted downward and cathodic (reduction) currents are plotted upward (See FIG. 11).

Figure 12:
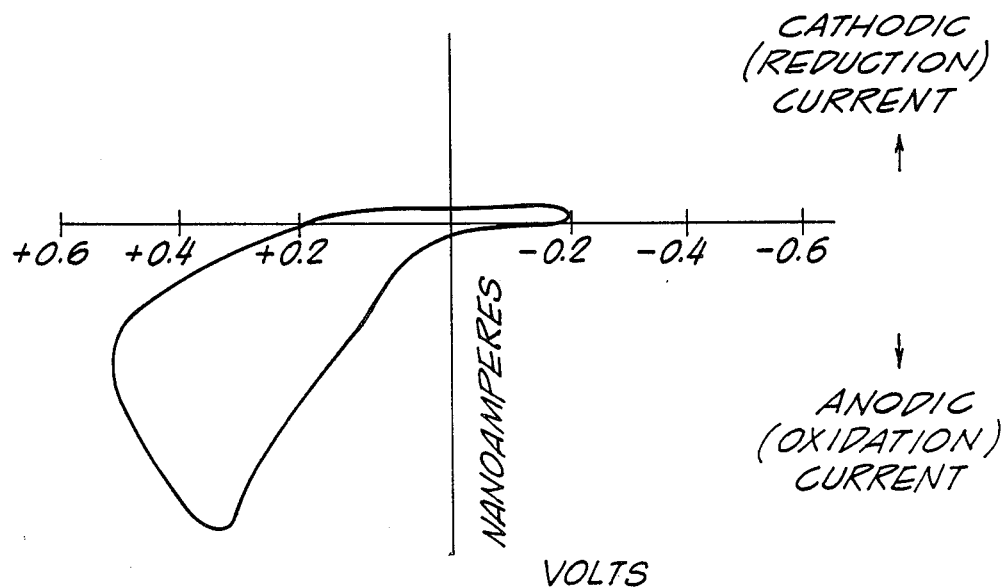
FIG. 12 is a representation of a typical linear scan cyclic voltammogram for an irreversible redox reaction producing a stable oxidized species only.

In the brain, in specific areas such as caudate, cerebral cortex and hippocampus, some biochemical reactions are irreversible in that they do not yield reproducible stable species, in range. This is indicated by the lack of reduced species on the reverse half cycle, as shown by FIG. 12, a linear scan cyclic voltammogram.

Figure 13:
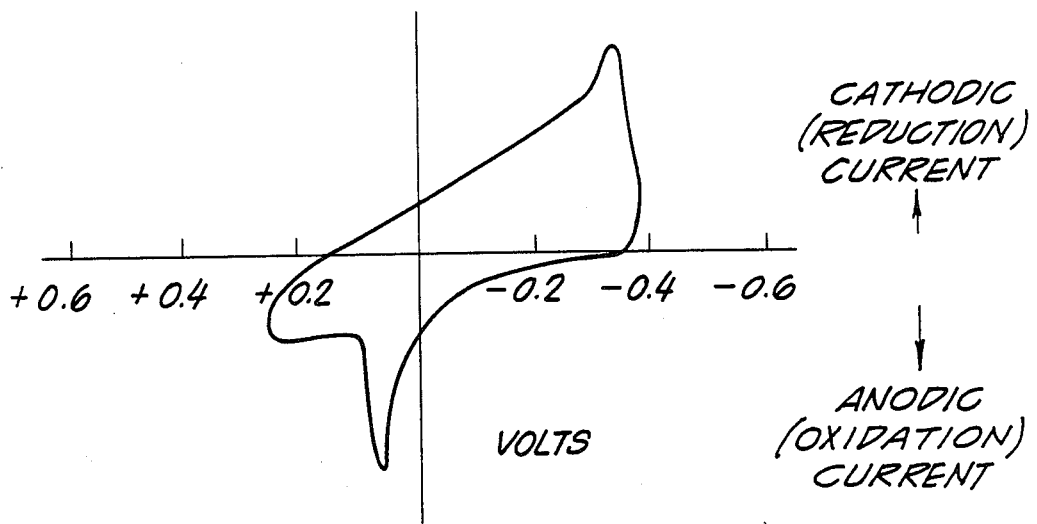
FIG. 13 is a representation of a typical linear scan cyclic voltammogram producing stable reduced and oxidized species.

Some organic material shows reversibility in brain tissue such as the oxidation-reduction behavior of injected 6-hydroxydopamine (6OHDA) and the injected quinone 6-hydroxyquinone (6OHQ). This reversible reaction produces both stable reduced species (6OHDA) and stable oxidized species (6OHQ). FIG. 13 illustrates this reaction as a linear scan. Peaks appear at the voltages at which these species are, respectively, reduced and oxidized. This is an example of the use of the apparatus of the prior art to measure an oxidation current.

The application of a potential between 0 and +1000 mv tests for stable oxidation species; application of a potential between 0 and −1000 mv detects reducible species. This is a useful test to distinguish reversible from irreversible oxidation reactions in all types of electrochemical experimentation.

An electrical circuit for providing an output signal having a mathematical relationship in operation to an input signal can be semiintegrated or semidifferentiated. The semiintegration circuit consists of an electrical transmission line in the input to the operational amplifier; the semidifferentiated circuit has such a line in the feedback loop of an operational amplifier.

Figure 14:
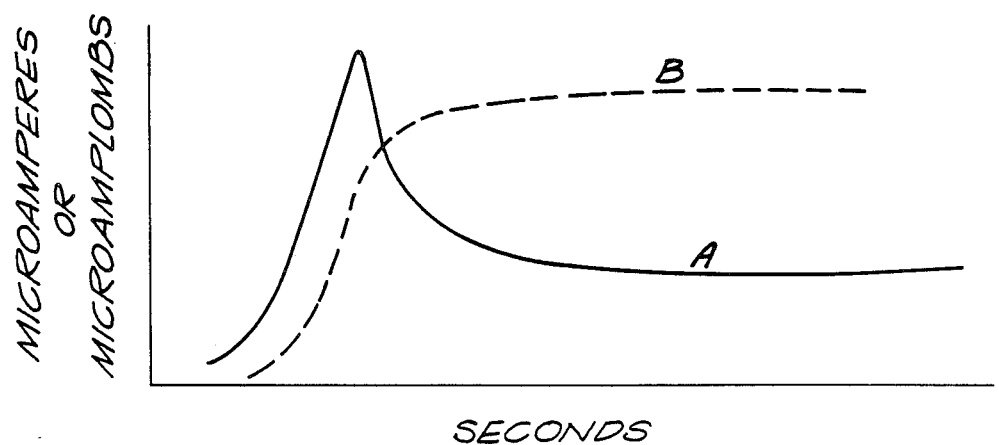
FIG. 14 is a representation of semiintegrated and semiderivative signals wherein curve A in amperes represents unchanged current and curve B in amplombs represents a semiintegrated curve, the latter providing for a longer lasting signal.

Semiintegral and semidifferential electroanalysis diminishes non-faradaic current by the addition of analysis time. A graph comparing results obtained from electroanalytical apparatus where the indicator (working) electrode current i(t) has been recorded (a) unchanged (Curve A in amperes) and (b) semi-integrated (Curve B in amplombs) is shown in FIG. 14. The amplomb measurement on the y-axis is the sum of ampere $sec^{\frac{1}{2}}$ and coulomb $sec^{\frac{1}{2}}$. The full current curve (A) contains a preliminary peak followed by a falling off, making integration difficult. However, the semiintegrated curve (B) rises to a steady state value which can be used to determine concentration in dynamic levels because the signal lasts longer than that of linear scanning techniques.

It is postulated that, due to the speed at which the semiderivative circuitry is able to process signals, the reduced and oxidized species in the brain are detected using cathodic current according to the method of this invention. Conventional brain electrochemical scans have only processed oxidation currents. It is a novel aspect of this invention that cathodic reduction currents can be used to detect neurotransmitters and other chemicals in the brain and other sub-organisms.

The method of this invention describes a circuitry which can differentiate specific chemicals as biological markers of diseased states for purposes of psychotherapeutics, i.e. irreversible and reversible substances in the diagnosis of mental disease such as Alzheimer's and schizophrenia, mood disorders relating to diseases such as diabetes, and peripheral disease such as uterine or cervical cancer, diabetes, and the subsequent application of the principles of telemetry thereof and the automation of the technique.

The method of this invention distinguishes semiintegral and semidifferential electroanalysis from other types of electrochemical analysis such as linear scan techniques within the concepts of cathodic and anodic currents. In the circuitry of the method of this invention, a cathodic (reduction) current is used to detect reversible and irreversible oxidizable and reducible species to delineate specific chemicals in disease vis-a-vis the anodic (oxidation) current taught in the prior art. Anodic currents taught in the prior art are unusable for semidifferential techniques in brain and other sub-organisms. They are unstable and not reproducible. Cathodic currents with semidifferential circuits are stable, reproducible and irreversible and not amenable to cyclic voltammetry. Another embodiment of the method of this ivention would be the insertion of a differential operational amplifier to process the first derivative of the output current so as to provide a signal that would be cyclic in nature. This could also be a signal inversion circuit.

When monitoring the reaction of biological systems to the administration of a particular stimulus, such as a drug, a baseline value should first be obtained by measuring the current generated with respect to different potentials without the stimulus. The voltammeter is used to obtain a baseline value for certain biogenic chemicals by measuring the current generated from the brain with respect to the application of varying potentials or voltages. Different potentials range from about −200 mv to about −1000 or from about 0 to about +1000 mv or any combination thereof may be applied. The scan rate, or rate at which the potentials are applied, is preferably in the range of about 5 to 30 mv-$sec^{-1}$, most preferably about 10 mv-$sec^{-1}$. Sensitivity, or amplification of the signal, can be in the range between about 0.1 and 10 $nA^{-\frac{1}{2}}cm^{-1}$, with time constants between about 0.001 and 10 seconds.

The reaction to the administration of a stimulus can be measured after baseline values are recorded. After administration of the stimulus, potentials are applied and the current is measured with respect to the changing potentials. A comparison between voltammograms obtained prior to and after the stimulus will indicate the changes in production of biogenic chemicals and hence the presence of diseased states even leading to bizarre behavior.

The method of this invention can be used for chronic studies, which take place over a relatively long time period, e.g. three to four months, or for acute studies in which values are taken over a short time period or only a few times.

Preferably, the reference electrode used should be of Ag/AgCl. The auxiliary electrode can be a platinum or a stainless steel electrode. Various modifications, however, may be made. The working electrode, if used for acute or chronic studies in a freely-moving animal, is preferably composed of a teflon-coated microelectrode homogeneously packed with graphite paste and nujol (mineral oil). This allows the subject to move without breaking the electrode. If used for acute or chronic studies in an anesthetized animal, either glass or stainless steel with a teflon coat electrodes may be used. If it is desired to measure biogenic chemicals without interference from certain acids such as ascorbic acid or the dopamine metabolite 3,4-dihydroxyphenylacetic acid, or to measure serotonin without uric acid or 5-hydroxyindoleacetic acid, the serotonin metabolite, the graphite paste should be modified. Blaha and Lane, in *Brain Research Bulletin*, Vol. 10, (1983) p. 861 have suggested modification with stearate. It is believed that the same selectivity can be achieved using Nafion-coated electrodes or other coatings known to those of ordinary skill in the art [Adams, 1984]. The fatty acids differ in the complex lipids which contain backbone structure to which the fatty acids are covalently joined. The paste may also be modified with fatty acids, fatty acid derivatives, such as arachadic acid and salts thereof and other complex lipids such as acylgylycerols, phosphoglycerides, sphingolipids and waxes, or additional perfluorosulfonated compounds. Stearate modification has been shown to detect serotonin without detecting 5- hydroxyindoleacetic acid or uric acid (Broderick, 1984, 1986). Various modifications on the indicator electrode can be made. The indicator electrode can be made a variable oxidant so that selectivity for anionic and cationic species can be made such that previously unidentified biological markers can be detected by electrostatic repulsion between the electrode surface and the molecule of interest.

Electrodes may be constructed as follows, but their construction is in no way limited to the method described herein: the Teflon coat of a stainless steel indicator electrode (tip diameter size 150 u consistently) can be pulled, 500 u, over stainless steel and packed with graphite paste. Stearic acid (100 mg) can be mixed with 1.5 g carbon power in 1 ml Nujol. This electrode treatment produces cationic selectivity which has been reported previously for dopamine (Blaha and Lane 1983) and for serotonin (Broderick 1983). Potentials were applied to the indicator electrode between $-200$ mv and $+500$ mv. The criteria for selection of appropriate indicator electrodes can be: (a) that the electrode showed at least 100 mv deflection with 10 uM DAHCL (dopamine hydrochloride); (b) that the paste composition presented homogeneously under a dissection microscope, 300 x magnification. The potentials were measured with respect to an AG/AgCl (1M NaCl) reference electrode.

The reference electrode can be fabricated by coating with chloride the entire length of a forty mm silver wire, previously coiled around an ⅛ inch drill bit. The chloride can then be coated in a 1M-NaCl solution for one-half hour at a current of 2 mA per electrode. The electrode is then equilibrated in fifty mL of a 1M-NaCl solution until the criterion for the reference electrode is satisfied, i.e. the potential difference between the fabricated reference electrode and a BAS reference electrode (not usable in brain) should not exceed 10 mv.

In addition, an auxiliary electrode, made of stainless steel, can be housed in combination with the reference Ag/AgCl electrode in a one ml Biotip brand pipette (Becton-Dickinson, Orangeburg, N.Y.).

Preferably, the electrodes are implanted in vivo using a stereotaxic surgery device such as the David Kopf device. A David Kopf device consists of pairs of microscaled bars which allow the surgeon to implant the electrodes at the precise organ site desired.

The method of this invention may be used to measure biogenic chemical levels, release or reuptake inhibition in synapses of both anesthetized animals or humans and freely-moving (unanesthetized) animals or humans.

The method of this invention may also be used to elucidate behavioral determinants. By determining the levels of release or reuptake of biogenic chemicals and the changes in those levels, release or reuptake, while observing certain animal and human behavior, one can correlate the behavior patterns with the biogenic chemical alterations. This observation can contribute to the possible determinations of the causes of certain behavioral studies in all stages of life (neonatal, adult and aged), for example, brain reward/brain pain systems, euphoria, drug addiction, alcohol dependency, diabetes, self-administration studies, stereotype, catalepsy, antianxiety or anxiety paradigms, turning behavior paradigms, reactions to environmental stimuli throughout life stages, conflict/avoidance paradigms, muricide, and other behavioral studies such as memory loss or brain injury, due to ischemia, stroke and other cardiovascular consequences.

The method of this invention can be used in vivo in applications involving any warm-blooded or cold-blooded animal possessing a brain or a primitive brain or type of brain and other organs of the body, such as a human, a primate, a lower mammal, reptile or squid. It is particularly well-adapted to observing the levels of biogenic chemicals in mammals, including human beings, which has been heretofore unachievable.

Telemetric measuring devices known to those skilled in the art may also be used to monitor current via radio and TV signals such that external electrodes need not be attached to a stationary source which would hinder movement of the subject during measurement. For example, the telemetric dual antenna described in U.S. Pat. No. 4,539,710 (Dinsmore) which is incorporated herein by reference may be used in the telemetric embodiment of the process of this invention for detection of electrochemical signals from the brain or other suborganisms of animals and humans.

Figure 15:
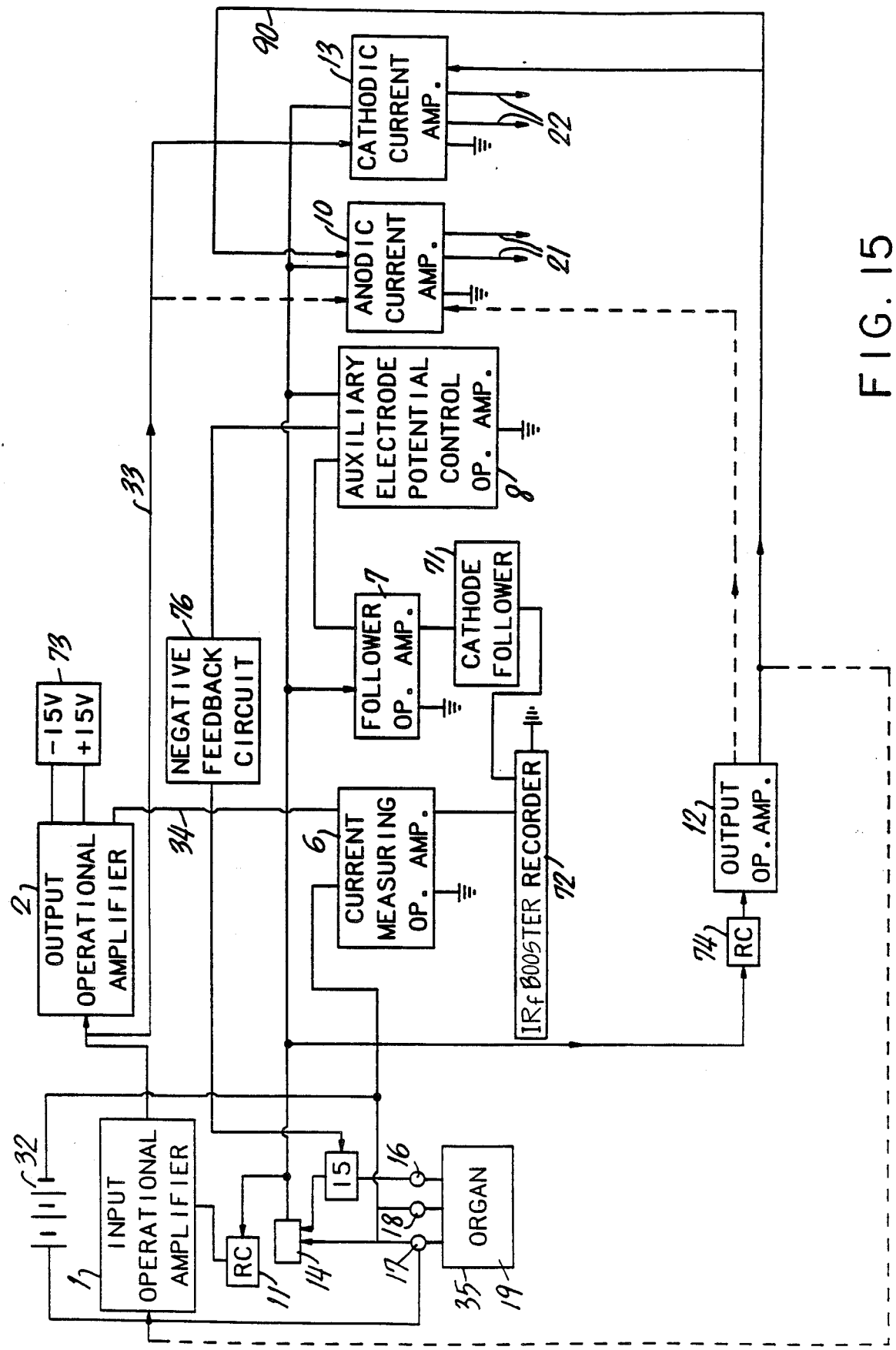
FIG. 15 is a schematic diagram illustrating an embodiment of a circuit arrangement according to the method of this invention. The diagram illustrates the circuitry for producing cathodic (reduction) currents to distinguish these from anodic (oxidation) currents which are used in other forms of electrochemical detection such as linear scan and chronoamperometry.
Figure 30:
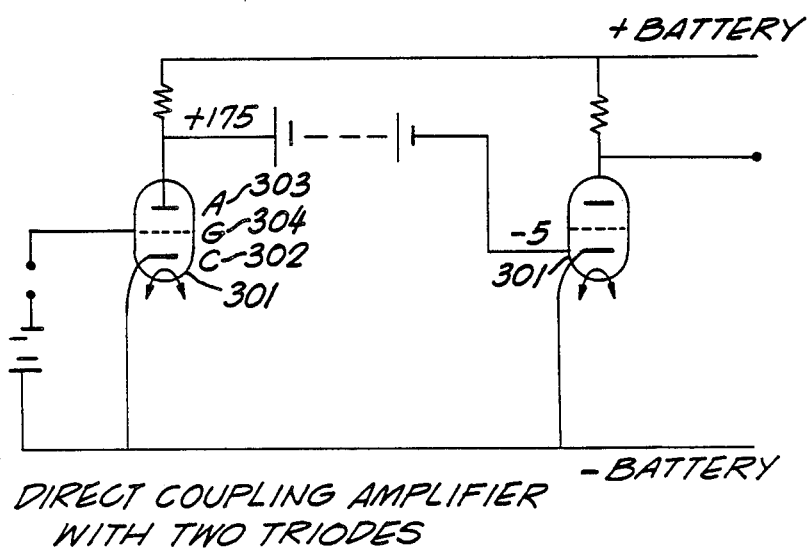
FIG. 30 is a schematic diagram of a direct coupling amplifier having two triodes.

The schematic diagram in FIG. 15 depicts the circuitry needed for the production of cathodic and anodic currents for semiintegral, semiderivative or semidifferential processing. An indicator electrode 17, reference electrode Ag/AgCl 16, and an auxiliary electrode 18 are connected to organ or sub-organ 19 and are connected to operational amplifiers, 14, 15 forming an electrochemical cell, 14–19. More specifically, operational amplifier 14 is connected between indicator electrode 17 and auxiliary electrode 18 and operational amplifier 15 is placed between reference electrode 16 and auxiliary electrode 18. The auxiliary electrode 18 and reference electrode 16 are placed in contact with the cortex or outer layer 35, of the organ or sub-organ. The indicator electrode 17 is inserted into the interior of the specific part of the brain or other suborganism which is the object of study. Battery 32 which provides an equal and opposite potential to that potential being measured is connected between the indicator electrode 17 and the reference electrode 16. A potentiostat (not shown) provides a known voltage against the electrochemical cell so that concentration changes at the electrode do not occur and so that no residual current will flow, causing an IR drop across the cell and changing the electromotive force. The circuit arrangement of the electrochemical cell, 14 to 18 is connected to operational amplifiers 6–8. The basic design of an operational amplifier is shown in FIG. 29. Operational amplifier 6 produces an analog signal proportional to the current through the indicator electrode 17 which is processed through a semidifferential ladder network which can be and is received by the y-axis external measuring instrument such as a recorder, 72. Operational amplifier 7 receives the analog voltage signal proportional to the current between electrodes 16 and 17 and the current is processed through a cathode follower, 71, which may be plotted on the x-axis of any recording instrument or an oscilloscope 72. Operational amplifier 8 maintains a constant potential on auxiliary electrode 18 by means of a negative feedback circuit 76 (not shown in detail) which automatically corrects for any drift of the potential difference between the reference and indicator electrodes. In accordance with the invention, the electrochemical cell 14–19 is connected in series with direct coupling amplifiers 10 and 13, which can be triodes or pentodes examples of which are seen in FIG. 30. Transistor amplifiers or integrated circuit amplifiers could, of course, also be used. These amplifiers respectively produce anodic and cathodic currents emitted from the organ being studied. RC filters 11 and 74 filter out unwanted and transient surges in electrical output. The resistance capacitance complex amplifier resists an exponential decay of signal. It is expressed as a time constant, in seconds. The time constant in seconds can be varied so that different components of the signal can be detected and interpreted. Differential operational amplifiers 1 and 2 are a ladder network of resistors and capacitors for semidifferentiating the current produced by the electrochemical cell. As stated previously, ladder network amplifiers such as 1 or 2 are described in the Oldham work, incorporated herein by reference. Ladder network amplifiers 1 and 2 are used to semidifferentiate cathodic (reduction) currents for the purposes of delineating irreversible and reversible biological chemicals and the like for medical diagnosis. Operational amplifier 1 transmits an input signal to operational amplifier 13 which like amplifier 10 may be a triode as shown in FIG. 30. The signal is then transmitted to terminal output cables 22 for direct processing of semidifferential cathodic current. One aspect of the novel circuitry is the electrical connection 33 between amplifiers 1 and 13.

Figure 16:
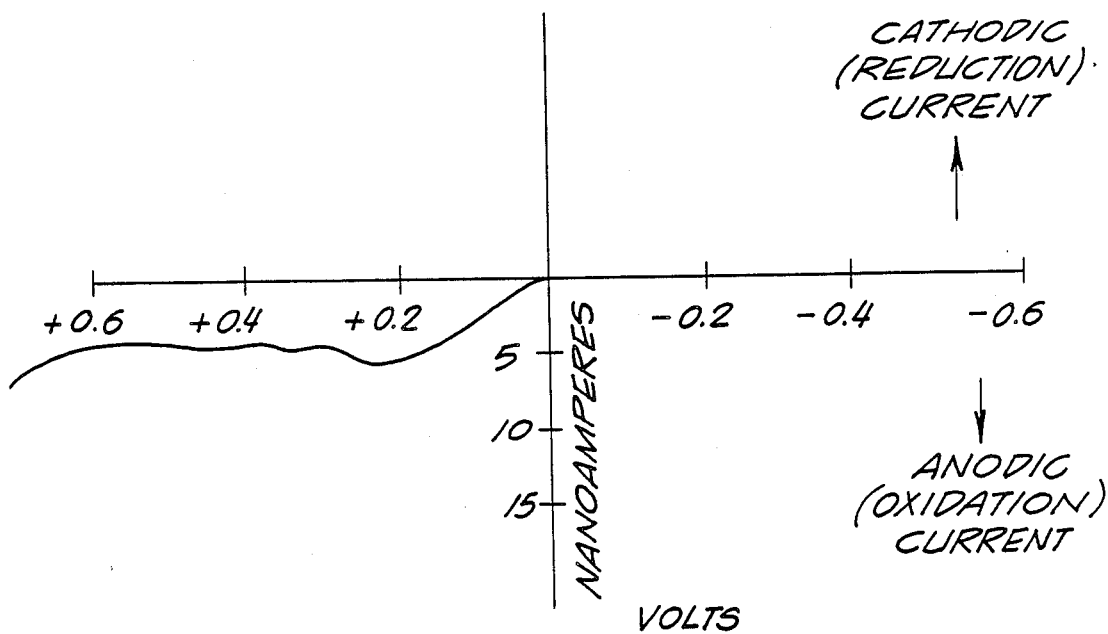
FIG. 16 is a diagram illustrating a linear scan voltammogram showing the production of biogenic chemicals using the conventional electrochemical notation.

Input operational amplifier 15 is connected between auxiliary electrode 18 and reference electrode 16 and to the input of output operational amplifier 12 through RC filter 74. Amplifier 12, which has an output connected to an input of cathodic current amplifier 13, may also optionally be connected so as to output to anodic current amplifier 10. Since amplifiers 10 and 12 have a linear gain, this arrangement will produce linear reproductions of the cathodic and anodic currents when a chart recorder such as 72 is connected to outputs of amplifiers 10 and 13. The linear scan is shown in FIG. 16.

Figure 10A:
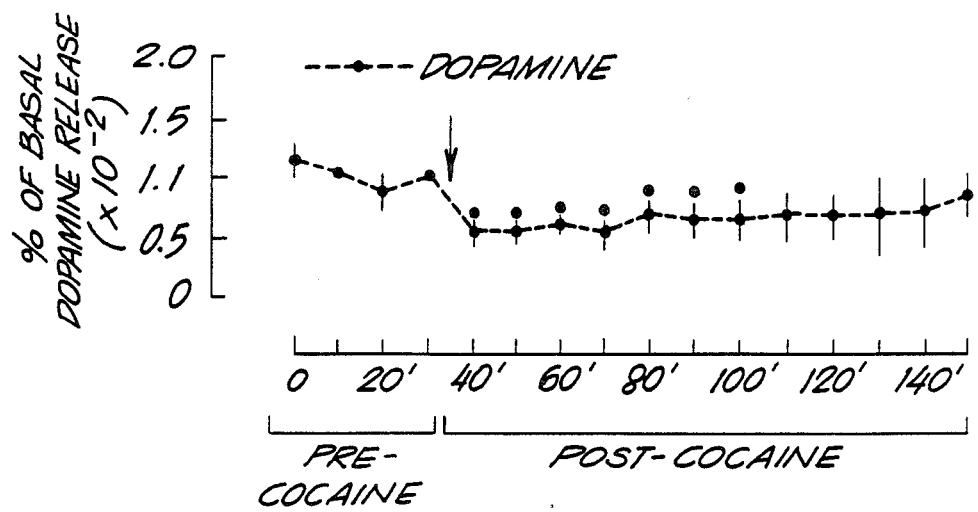
FIG. 10A illustrates a line graph showing the time course characteristics of the effect of cocaine (20 mg/kg injected subcutaneously ) on dopamine release from rat striatum. The x axis represents time (in minutes) before and after the administration of cocaine. The y axis represents dopamine release as percent of control. The percent of controls were calculated by averaging the first four scans and dividing all values by that average.
Figure 10B:
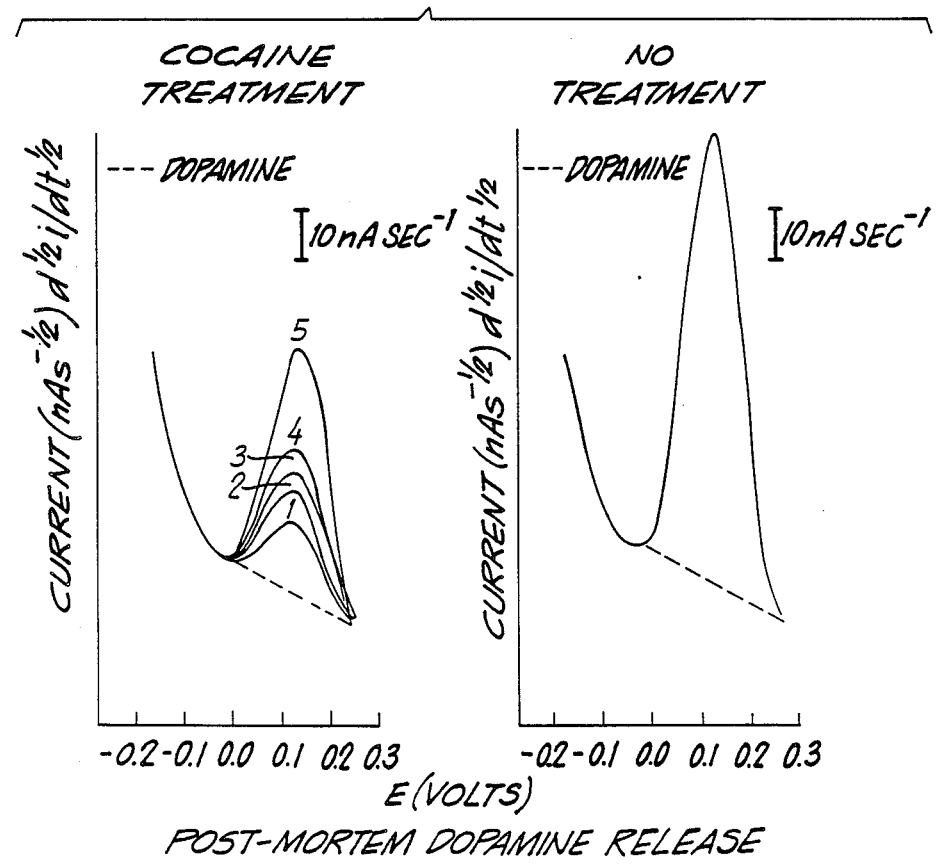
FIG. 10B illustrates semiderivative voltammograms showing post-mortem differences between dopamine release in cocaine treated (left voltammogram) and untreated animals (right voltammogram). The x axis represents increasing oxidation potentials in volts; the y axis represents current in nA sec$^{-1}$. The electrochemical signal for dopamine (1) represents dopamine release pre-mortem. The electrochemical signals for dopamine (2,3,4,5) represent dopamine release post-mortem, (ten minute intervals), in a cocaine treated animal. In contrast, the right voltammogram represents dopamine release ten minutes post-mortem in an untreated animal. The figure uses nonconventional electrochemical notation.
Figure 17:
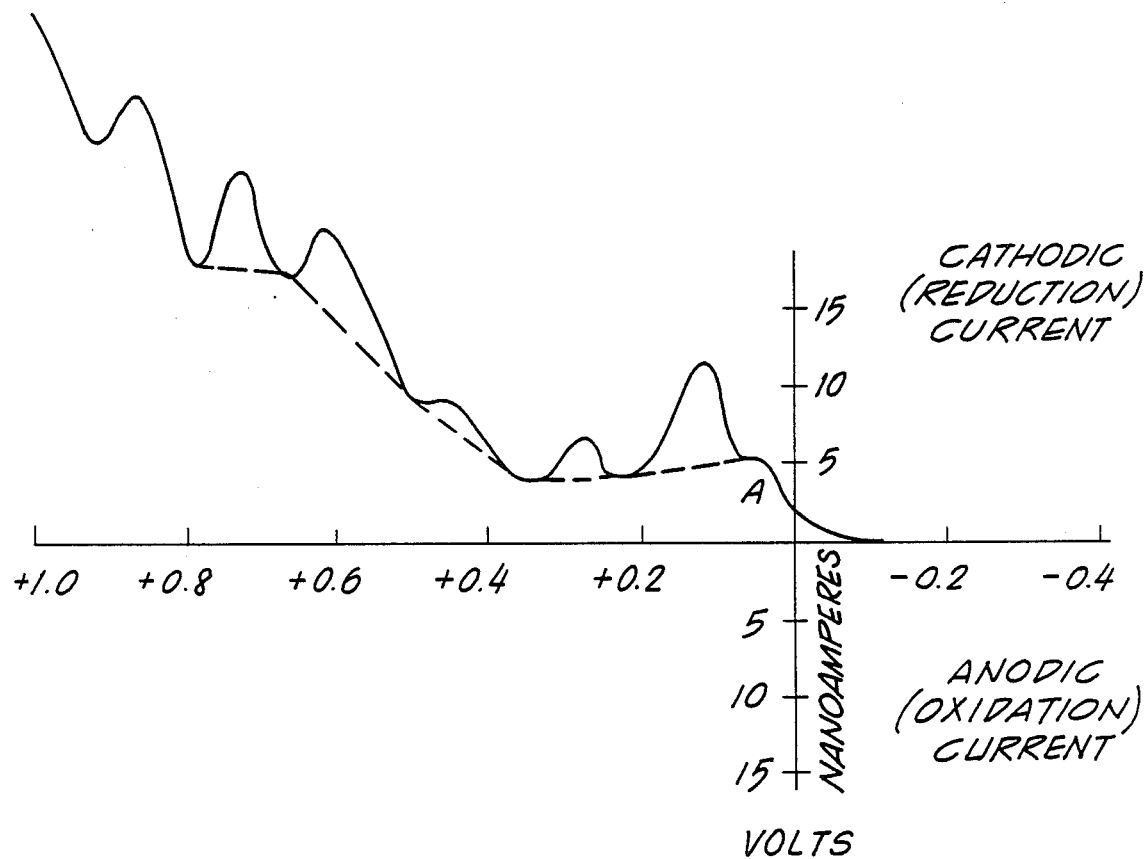
FIG. 17 illustrates a semidifferential voltammogram showing the production of biogenic chemicals peaks at 150, 290, 520, 690, 790, 820 and 910 mv. This Figure illustrates the usefulness of the methods of this invention in medical diagnosis, as the peaks represent neurotransmitter and neurotransmitter-like peptides as detected by cathodic currents in accordance with the method of this invention with semidifferential processing according to the invention herein using conventional electrochemical notation and describing peaks not heretofore described.

Optionally (connections not shown) an output of amplifier 12 can be connected to an input of semidifferential amplifier 1 and then the output obtained from amplifier 1 can be connected to the input of amplifier 13 to result in a signal having a steeper slope of current versus oxidation potential as shown in FIG. 17. This signal has the advantage of more clearly defining the chemicals being analyzed and increasing the time for analysis as shown in FIG. 10b. The output of amplifier 2 can be directly connected to the y-axis of the recorder 72 by line 34.

Power supply 73, which is shown providing plus fifteen and minus fifteen volts to semidifferential amplifier 2, may also be used as a power supply for linear operational amplifier 12.

Alternatively, in place of the electrical connection between 1 and 13, a potential divider circuit with a triode or transistor selecting switch (not shown) can be used to direct the anodic current for non-differentiated and nonsemidifferentiated scanning techniques to triode operational amplifier 10 by connection line 90, in series with terminal output cables, 21. The potential divider circuit with an anode/cathode (triode) selecting switch can also be used to direct cathodic current for differentiated and semidifferentiated scanning techniques to the reduction amplifier, 13, in series with the terminal output cables, 22. A electrical connection line between amplifier 1 and triode 10, will provide results that are not confusing for currents that are non-differentiated. However, confusing results for current production that is differentiated or semidifferentiated will occur.

Figure 19:
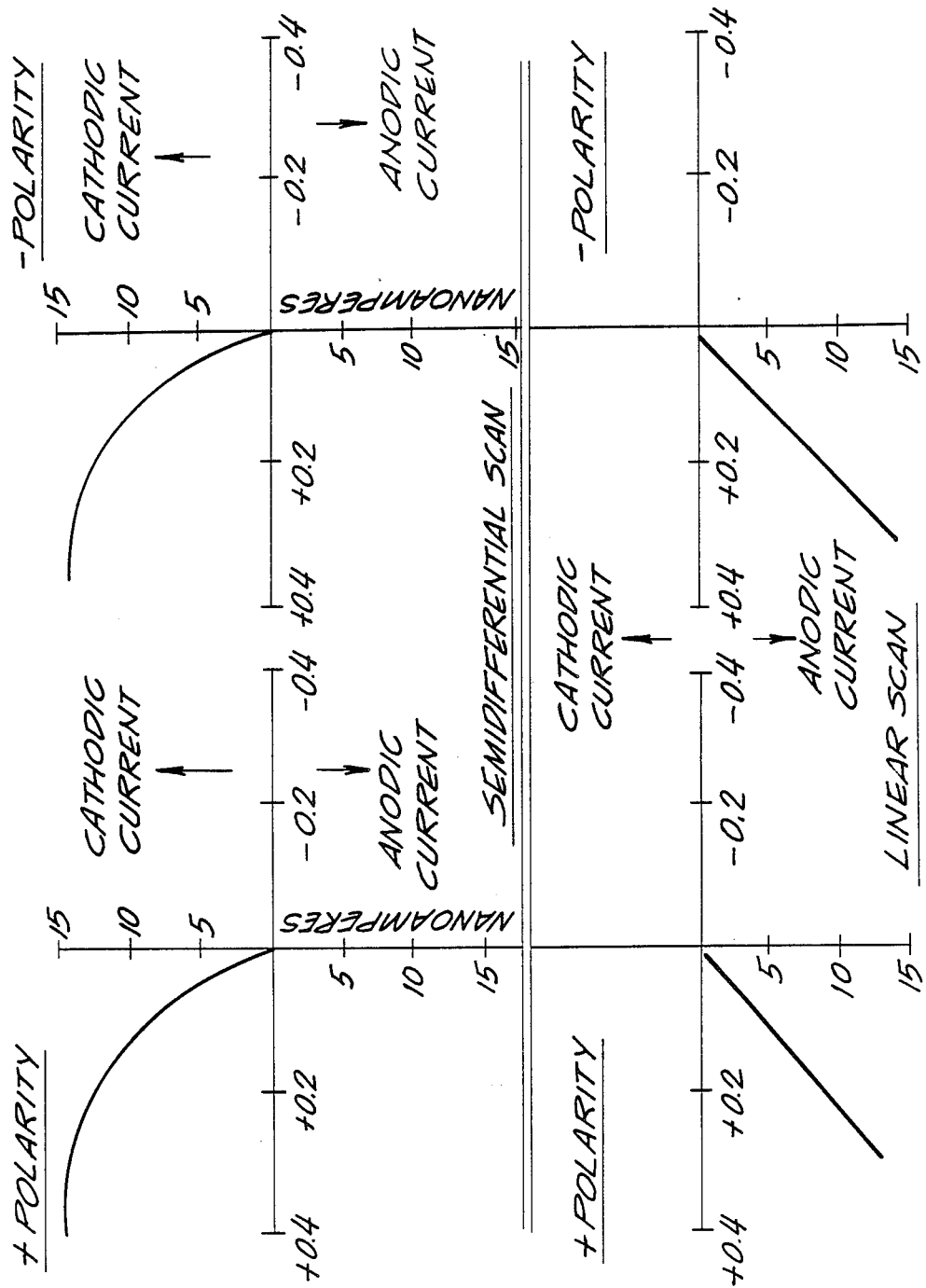
FIGS. 19(a) and 19(b) are diagrams illustrating that the difference between linear scanning techniques (b) and semiintegral and semidifferential processing (a) of current are not a function of polarity.
Figure 20A:
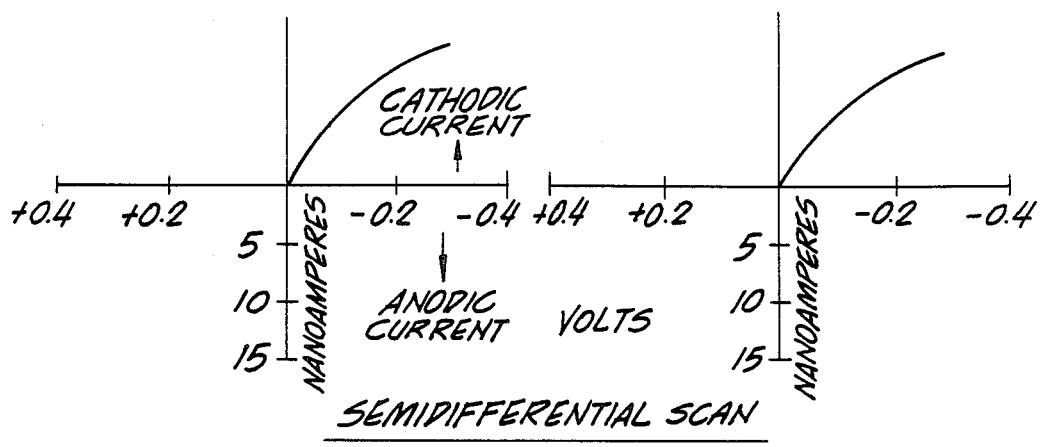
FIGS. 20(a) and 20(b) are diagrams illustrating that the differences between linear scanning techniques (b) and semiintegral and semidifferential processing (a) of current are not a function of the directionality of Eapp (applied potential).
Figure 20B:
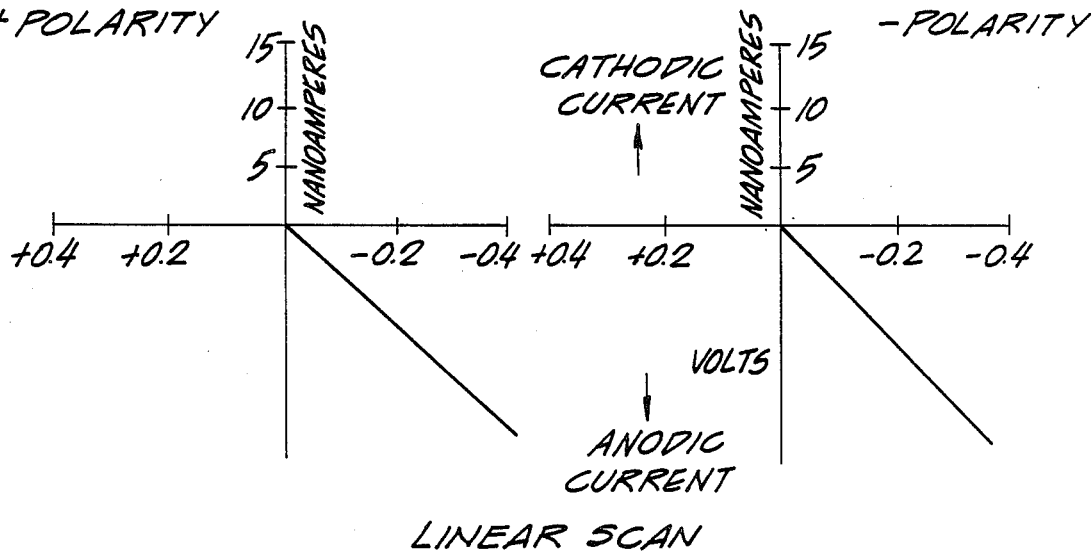
Figure 21:
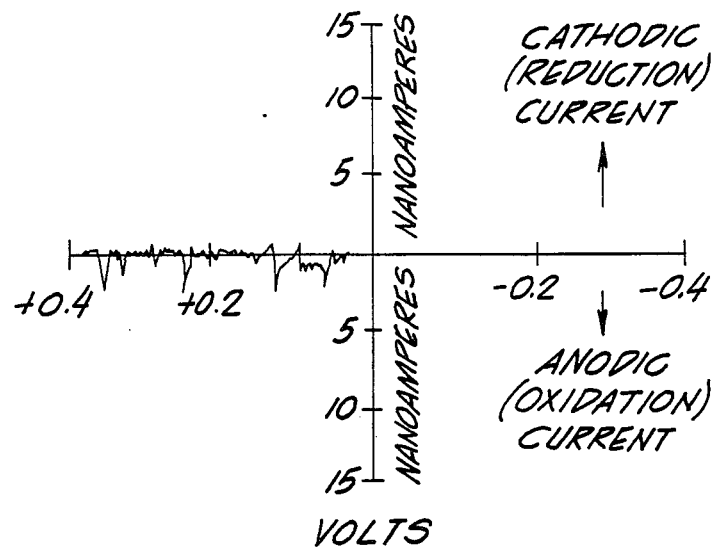
FIG. 21 is a diagram illustrating recording results from a semidifferential voltammogram processed with an anodic (oxidation) current, from the brain. The recording is unrecognizable.
Figure 22:
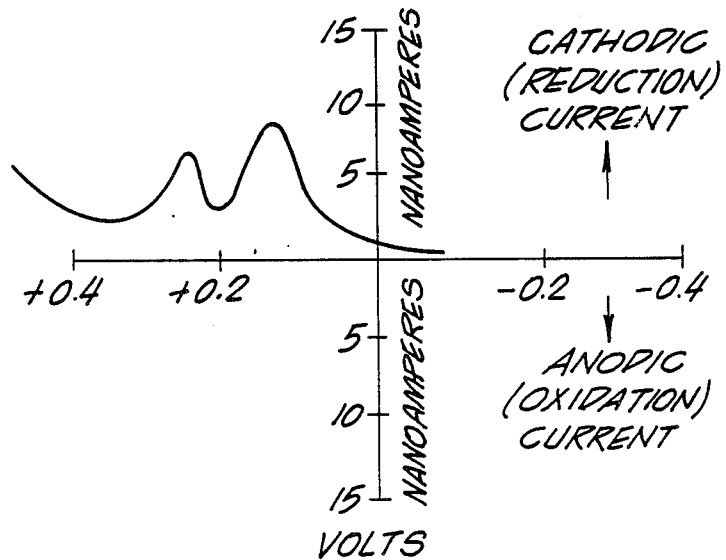
FIG. 22 is a diagram illustrating a recording from a semidifferential voltammogram processed with a cathodic (reduction) current according to the method of this invention.
Figure 23:
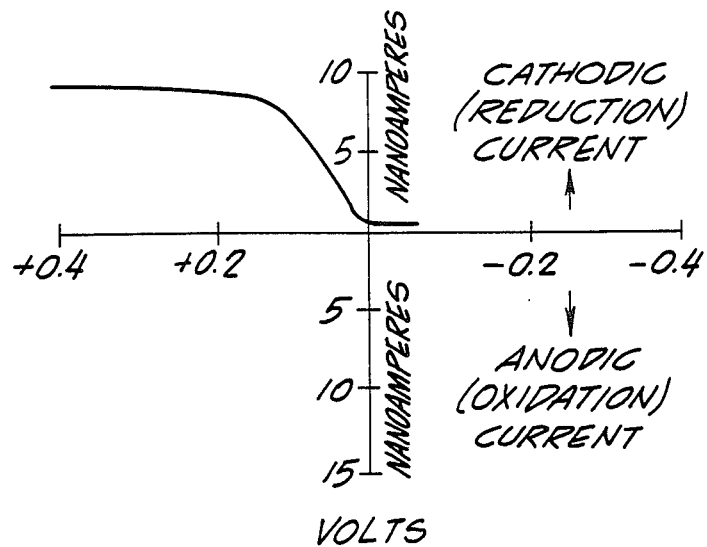
FIG. 23 is a diagram illustrating a recording from a semidifferential voltammogram processed with a cathodic (reduction) current with an electrode which had not been brain-treated; e.g., whose adsorption properties at the diffuse double layer of the electrode surface, the capacitance or barrier layer had not overcome the column effect.
Figure 24:
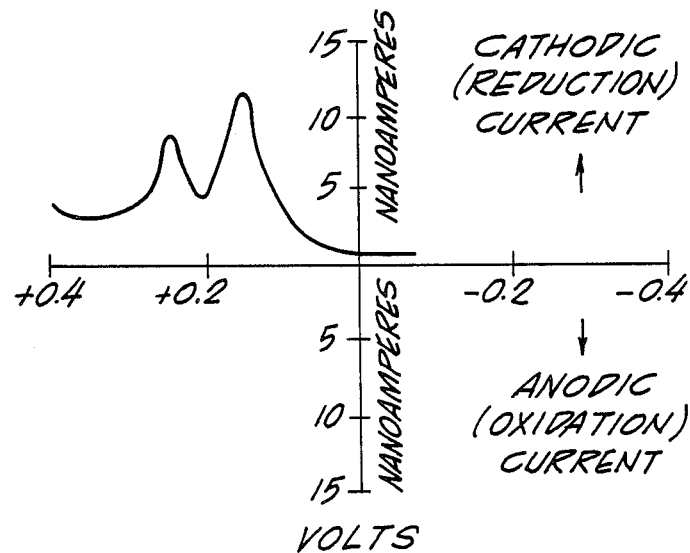
FIG. 24 is a diagram illustrating a recording from a semidifferential voltammogram, processed with a cathodic (reduction) current, with a brain fluid-adsorbed electrode treated with fatty acids to selectively detect cations or anions for medical diagnosis.
Figure 25:
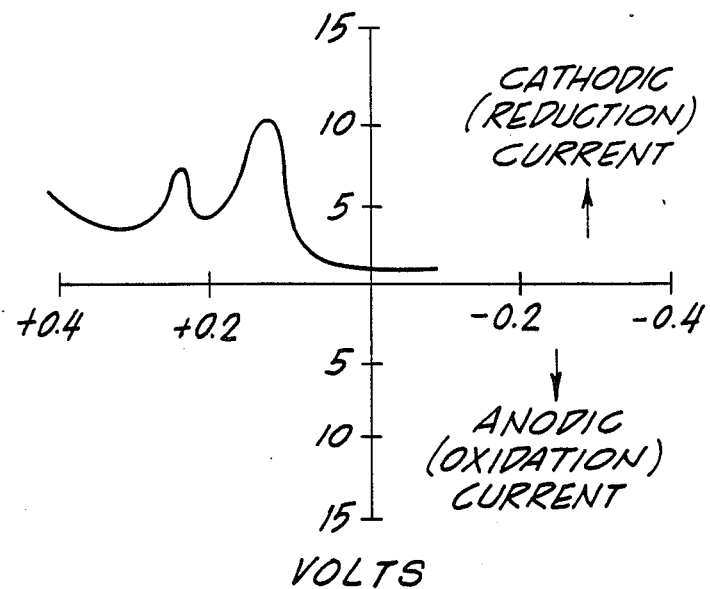
FIG. 25 is a diagram illustrating a recording from a semidifferential voltammogram, processed with a cathodic (reduction) current according to the method of this invention, with a brain fluid absorbed electrode, treated with fatty acids, in vitro in phosphate buffer (0.01M $PO_4$ buffer made with monobasic and dibasic phosphate) with dopamine and serotonin hydrochloride, said biogenic chemicals correlating to the same peaks in the brain, thus showing the detection of said biogenic chemicals as attainable for purposes of future discoveries in treatment.

The method of this invention requires a cathodic current production. This current production is not a simple function of a change in polarity, which would produce the same signal, as shown by FIG. 19; nor is it a simple function of the directionality of the applied potential, $E_{app}$, as shown by FIG. 20. FIG. 16 is a graphical representation of the use of anodic current used with non-differentiated current. FIG. 17 is a graphical representation of the use of the method of this invention; cathodic current used with semidifferentiated current. The graph of FIG. 17 shows sharp peaks produced by chemical species, compared to the curve generated by non-differentiated anodic current of FIG. 16.

Figure 18:
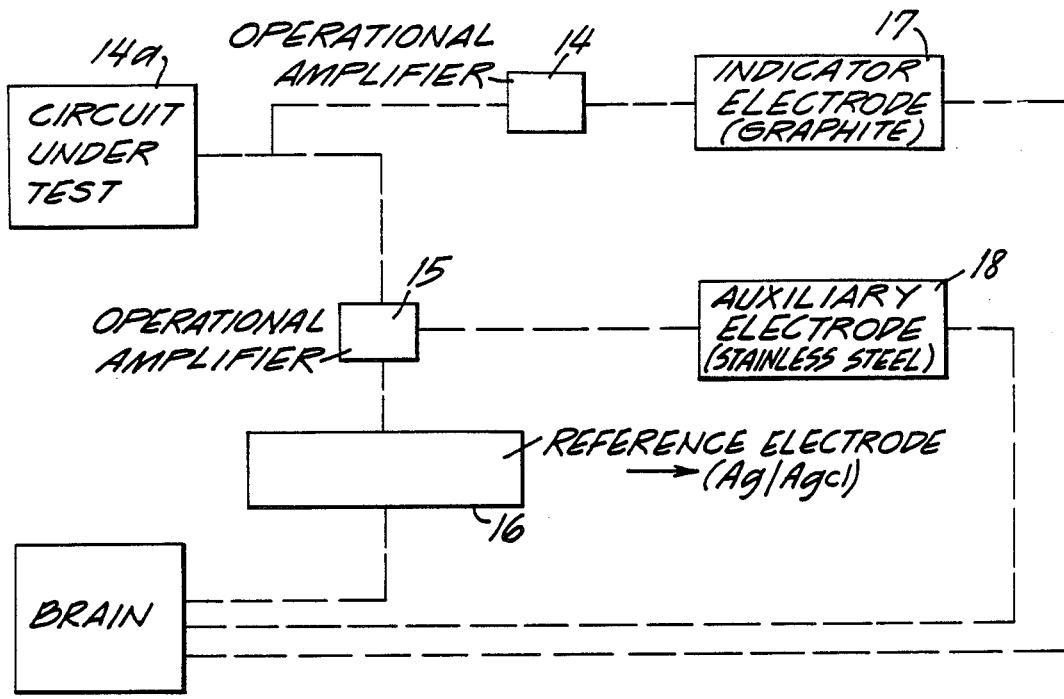
FIG. 18 is a schematic diagram of the three electrode system used in accordance with the method of this invention to generate such signals from living organisms and its relationship to the operational amplifier circuitry needed for semidifferential processing of current in addition to other types of electroanalysis.

FIG. 18 is a schematic diagram of the three electrode system necessary to generate electrochemical signals from brain and other parts of living and non-living things. The figure is drawn in relationship to said operational amplifier circuitry needed for varying types of electrochemical procedures. FIGS. 21 through 25 are graphical representations of correct electrochemical signals vis-a-vis incorrect electrochemical signals; only the correct signals are useful as markers for diseased and healthy states and are thereby useful for diagnostic and therapeutic medical research.

Figure 26:
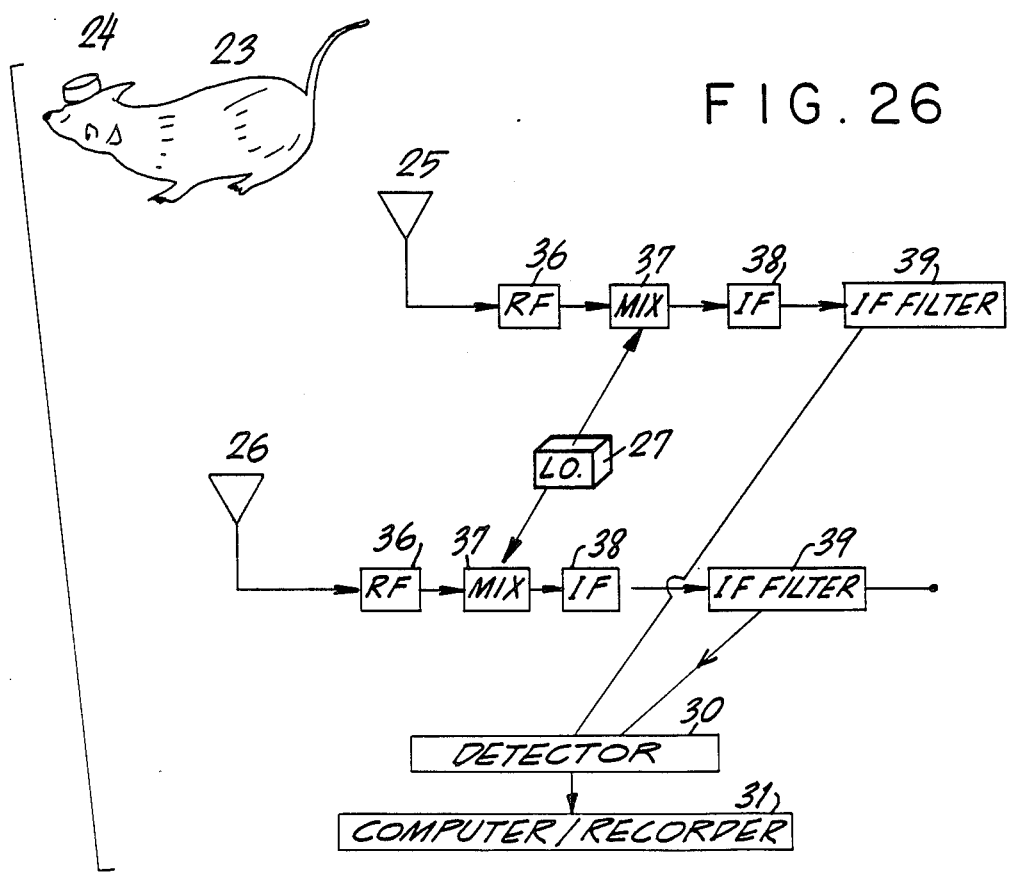
FIG. 26 is a schematic drawing illustrating the telemetric application to the electrochemical process of this invention, using a channel 8 or 9 television band in the transmitter to detect biogenic and other chemicals useful in biomedical diagnosis.

FIG. 26 shows the telemetric embodiment of the in vivo electrochemical semidifferential and linear detection of neurochemicals, biogenic amines and peptides both in the mobile and non-mobile, human and non-human organism, for purposes of medical diagnostics and preclinical and clinical pharmacotherapeutic discovery. Shown at, 23, is a pictorial view illustrating a rat, a commonly used laboratory animal, bred for the expressed purposes of biomedical research. The three electrode electrochemical circuit is implanted in the brain described in this invention, FIG. 18. The electrode system is then cemented to the skull of the organism with acrylic and fitted with a snap on telemetric transmitter, 24, the principal elements of which comprise a Channel 8 or 9 TV Band, an oscillator, a silver oxide battery power supply, a contact switch assembly and a contactor for the three electrode snap on closure electrode system. Voltage is transmitted via electrolytes in the brain extracellular fluid, to a dual antenna network, 25–27, according to the invention of Dinsmore which allows interference-free reception of physiological signals through telemetry. A plurality of RFFM receiving channels are each associated with an antenna. Each is comprised of one or more RF amplification stages 36, a mixer stage 37 and one or more intermediate frequency stages 38, 39 along with an analog circuit. The common local oscillator, 27, provides uniformity in the intermediate frequency. A current measurer operational amplifier changes the output voltage of the telemetric receiver to current by an analog circuit 30, and the signal is displayed on a computer printer or strip chart recorder, 31. The detector, 30, is preferably a 3089 IC from National Semiconductor Corporation in accordance with the method of Dinsmore, in combination with the semidifferential circuit of Oldham, in addition to the novel circuitry of this invention described in FIG. 15.

Figure 27:
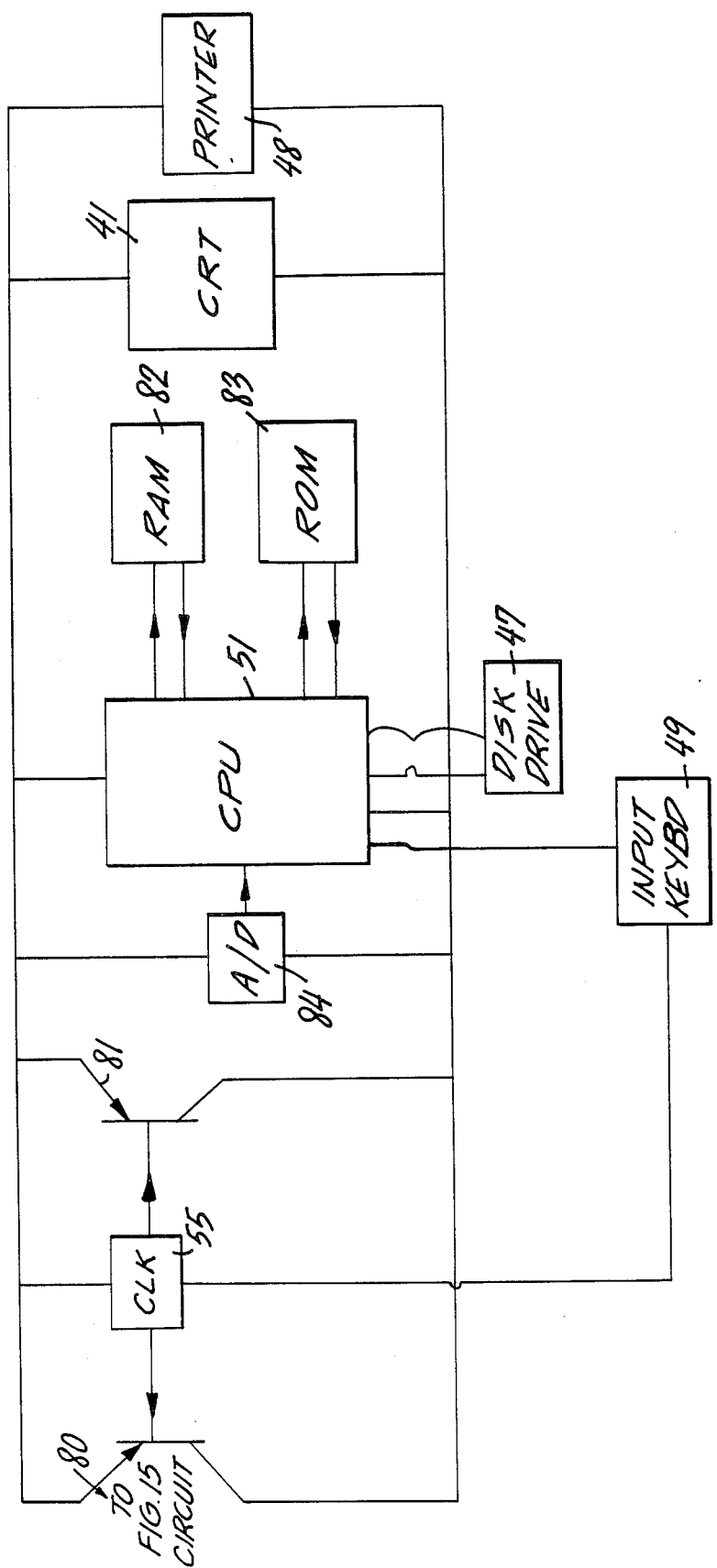
FIG. 27 is a schematic drawing illustrating a system for interfacing the detector with a computer.

The automation of the method of this invention to aid in the rapid detection of healthy and diseased states is described. A computer monitor, 41, a disk drive, 47, a printer, 48 and a computer keyboard, 49, are depicted in FIG. 27. Processor memory 82 and 83 are provided to move information from disk drive to memory. Memory disk drive 47 is provided as a means for bussing information. Chipboard 51 contains chips for the central processing unit, a fast 8-bit microprocessor, controlling analog to digital converter function, 84, printer 48 and disk drive 47. The "transistor-transistor logic", or "TTL", produces the outputs to the remote control pins of the circuitry depicted in FIG. 15. The output of organ 19 is connected to a detector (not shown) which contains all of the circuitry of FIG. 15. The TTL outputs can be controlled by an internal clock 55 such as the clock in an Apple IIe. The principal concept governing this automatic embodiment of the method of this invention is the application of the passage of a high voltage through a transistor in the computer TTL, 81, forming an on/off switch mechanism. The TTL logic is based on a switch which varies potential from 0 to 5 volts logic. The detector logic comprising the unamplified circuit of FIG. 15 is TTL also, based on a 0-5 Volts switch off/on logic. In a practical embodiment, a strap cable can connect computer TTL switch 81 with detector TTL switch 80 through a terminal strip, with an interfacing device (not shown) which receives inputs and outputs from the TTL 80 and the TTL 81. In the present invention, this interfacing device has no electronic importance, but that does not by any means preclude additional electronic importance in the future, e.g. operational amplifiers, intended to amplify or dampen, are contained in this box which could amplify or dampen or otherwise attenuate or amplify signals from the brain and other living sub-organisms should the electrical interference from, say several computers, serve to dampen the signal. A strap cable from the TTL 80 connector, electrically connected to cell 14-19 of FIG. 15 comprises five single cables, designated to ground, scanning operation, cell and beginning applied potential in mv. TTL inputs and outputs on A/D converter 84 direct analog to digital converter TTL Logic in the interface (not shown) and switch 80. In addition, the attached programs e.g. shown in FIGS. 28(a) and 28(b) integrate the height and area under each analog signal which emanates from the brain and/or other sub-organisms, thus allowing for on-line analysis of neurotransmitter- and neurotransmitter-like substances in healthy and diseased states for the purposes of medical diagnosis.

FIGS. 29 and 30 set forth preferred embodiments for accomplishing specific functions of the circuit of this invention as shown schematically in FIG. 15. In FIG. 29(a), $Z_1$ and $Z_2$ are feed-in and feed-back impedances and, when the amplifier is equipped with high gain capacitance, the transfer function of the circuit can be delineated by $Z_1$ and $Z_2$. The point B where $Z_1$ and $Z_2$ are connected together and to the amplifier input is the "summing junction," which provides a ground because the signal voltage is infinitesimal. The current through $Z_1$ is equal to the current through $Z_2$. V, the potential drop across C is defined as: $V = -1/c$ $$\int i\, dt = \frac{-1}{CR} \int V i\, dt.$$

FIG. 30 shows a type of direct coupling amplifier based on a triode 301, i.e. an electronic valve with a wire mesh grid 304 and a cathode 302. The triode is the basis of the amplifier. When one holds the third electrode (anode) 303 is held at a small negative potential relative to the cathode, electrons flowing through the valve are not attracted to the grid 304 but can still pass through it to the anode. Any change of the grid potential will produce a far greater change in the electrical field close to the cathode than will a similar alteration of anode potential. The direct coupling of more than one amplifier circuit allows the output of the first amplifier to be applied between the cathode and the grid of the next. The grid of the next stage should be held at a small negative potential with respect to its own cathode, to be a cathodic amplifier. A battery can provide a potential difference between the anode and the succeeding grid.

Figure 3A:
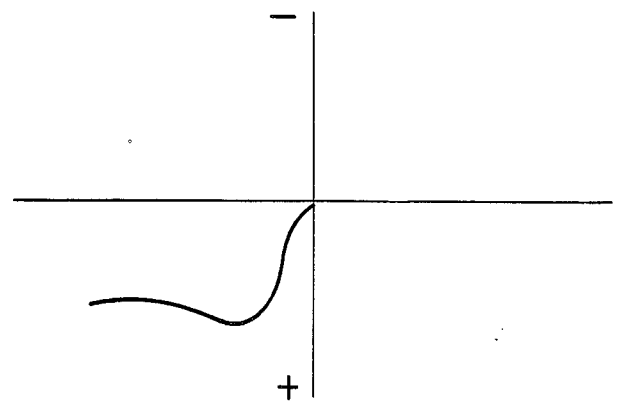
FIGS. 3A, 3B and 3C are representations of graphs showing signals which may be generated by linear and semidifferential scanning.
Figure 3B:
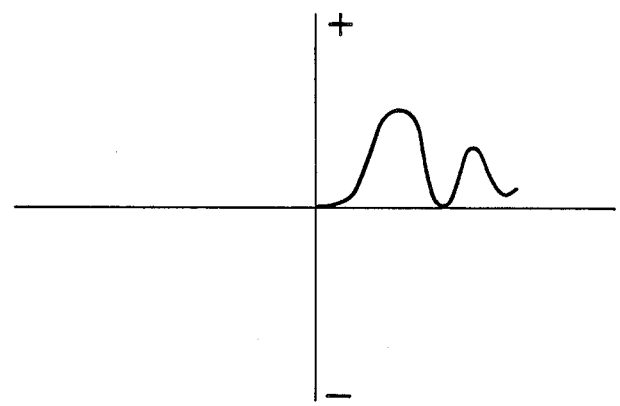
Figure 3C:
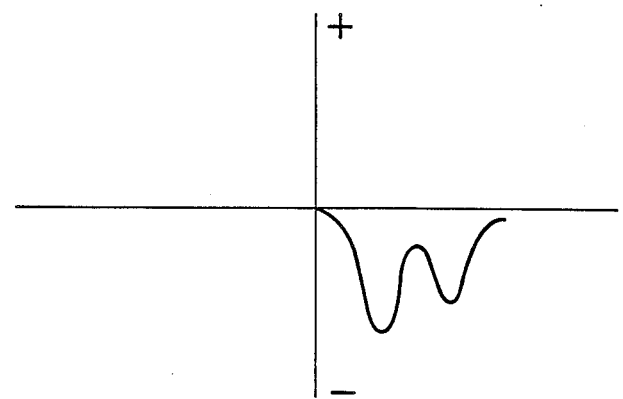

Therefore, one of the differences between the method of this invention and prior art methods can be seen by comparing a semiderivative voltammogram produced by using the method of this invention with graphs produced by prior art methods. In FIGS. 3A-3C, a "minus" notation denotes a reduction current and a "plus" notation denotes an oxidation current. FIG. 3A shows a graph obtained by a linear scan of biogenic chemicals. It is a typical curve representing an anodic current in conventional electrochemical form [Kissinger et al.]. In FIG. 3A, the peaks for biogenic amines, such as serotonin, are masked and undifferentiated from each other such as the dopamine peak. FIG. 3B is a semiderivative voltammogram which also presents an anodic current but is presented in non-conventional electrochemical form. [Lane, Hubbard and Blaha, J. Electrochemistry, Vol. 95, (1979, p. 117.) In FIG. 3B, the dopamine and serotonin signals are contaminated by many other amines and many metabolites in addition to ascorbic acid and possibly uric acid. FIG. 3B shows differentiated serotonin and dopamine peaks. FIG. 3C is a representation of a semiderivative voltammogram using nonconventional electrochemical notation, derived from using the method of this invention. It shows sharp, differentiated uncontaminated serotonin and dopamine peaks using a cathodic current and selective electrodes that are brain treated. Unexpectedly, these and other chemicals heretofore undescribed can be reproducibly detected, such as in FIG. 17, by using a cathodic current according to the method of this invention.

Thus, the reproducibility and purity of signals generated by the process of this invention allow the automation of the cathodic current as demonstrated in FIGS. 27 and 28, as well as the telemetric application of the process of this invention to aid in the diagnosis of diseased states as shown in FIG. 26.

The process of this invention may also be used in humans as a neurochemical mapping device in order to show electrode placement in the human brain. By knowing the typical signal pattern produced in each part of the brain, a physician or researcher would be aware of the exact location of the electrode in a living patient without the necessity of dissecting the brain.

Figures 5A, 5B:
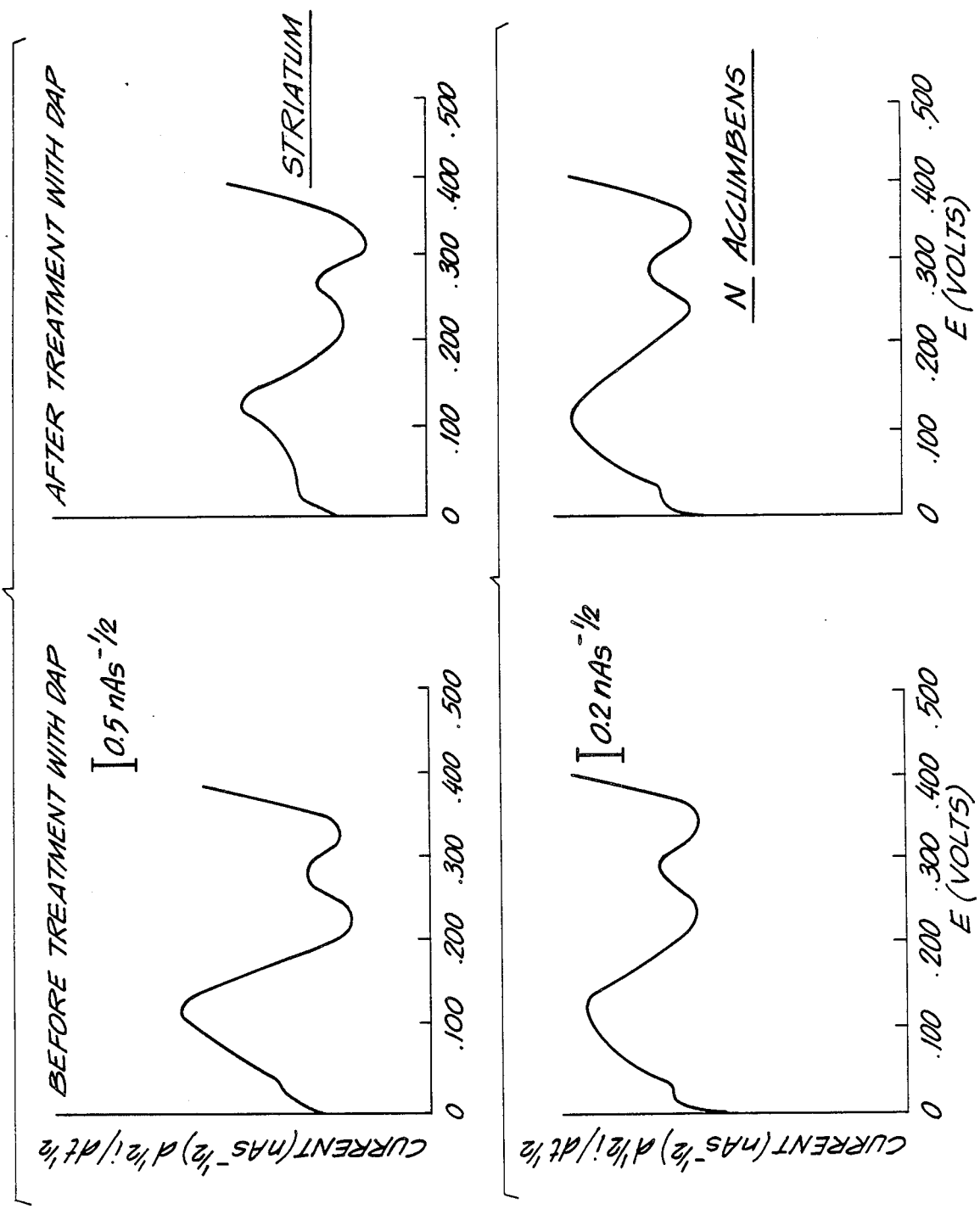
FIG. 5 is a representation of semiderivative voltammograms obtained from nucleus accumbens and striatum of the rat brain before and after treatment with DAP. These neurochemical profiles from different brain regions provide a means for neurochemical mapping for diagnosis as also exemplified in FIGS. 6 and 7, below, so that the electrode placement can be ascertained by the signal profile displayed on a recorder, printer, or computer monitor.
Figure 6:
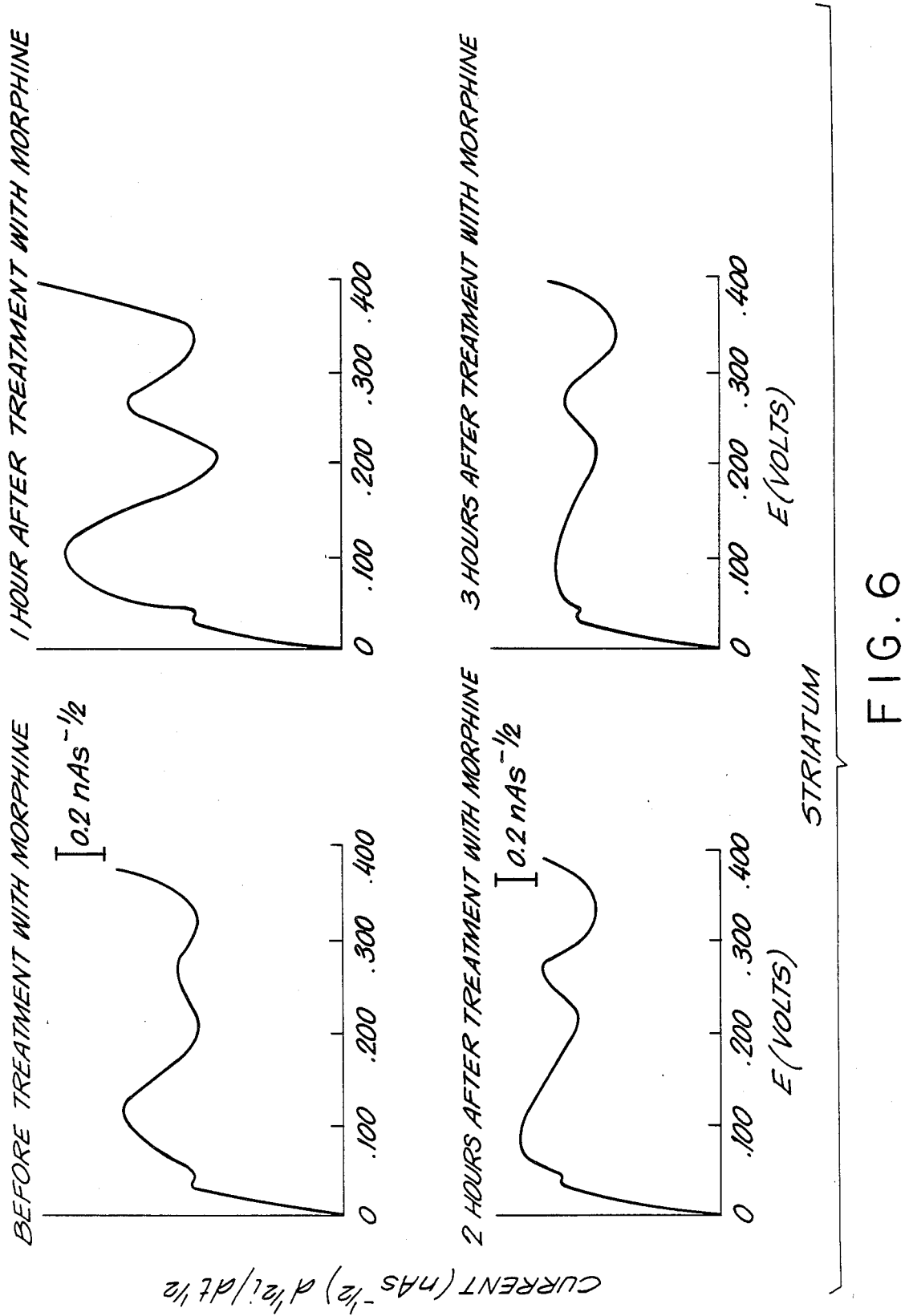
FIG. 6 is a representation of semiderivative voltammograms obtained prior to and 1, 2 and 3 hours after treatment with morphine, the results being directly related to underlying neurochemical addiction and pain processes.

The method of this invention can be used to measure biogenic chemicals in the organs of the body as well as in different parts of the brain, e.g. the striatum, tuberculum olfactorium, nucleus accumbens, median raphe, periaquaductal gray, hippocampus, locus coeruleus, the frontal cortex, amygdala, hypothalamus, thalamus, substantia nigra, globus pallidus and other areas. The methods of this invention can also be used to measure biogenic chemicals in such organs of the body as the heart, the retina, the gut, the cervix, kidney, liver, gall bladder, vagina and the like so as to diagnosis, e.g., cervical cancer and the like. Subsequent neurochemical profiles are useful in diagnosis. For example, the method can also be used as a mapping device to determine electrode placement in the human, as shown in FIGS. 5, 6 and 7.

Moreover, it can be used as a diagnostic tool to measure dynamic levels of biogenic chemicals and compare them to established normal dynamic values. The method of this invention can be used to measure levels of biogenic chemicals such as amines, amine metabolites, ascorbic acid, amino acids, particularly dopamine, homovanillic acid, tryptophan (a chemically irreversible substance), serotonin, enkephalins and enkephalinamides. It is believed that neuropeptides can also be measured using the method of this invention.

It is also believed that non-electroactive substances such as acetylcholine and electroactive substances that have small diffusion coefficients can be measured using the method of this invention. Non-electroactive substances and electroactive substances with small diffusion coefficients as well as electroactive substances having more than one electroactive moiety could be detected by immunoassay. An antigen would be bound to an antibody and injected iontophoretically into brain tissue. Free and bound antigen would differ in their electrochemical characteristics and cause the detection of new substances. U.S. Pat. No. 4,395,312, issued Jul. 16, 1983 to McCreery discusses similar means to effect detection of some biochemical species in vitro.

These chemicals may be present at certain dynamic levels in normal persons without the administration of any stimuli. However, in persons having abnormal psychological characteristics, and, therefore, forms of mental illness, different dynamic levels of biogenic chemicals may be present. Thus, the in vivo electrochemical method of this invention may be used to diagnose mental illnesses, such as obesity, depression, manic depression, drug addiction, and others, according to the dynamic levels of certain chemicals in the brain. The method of this invention can also be used for predicting the advent of neurological and other diseases such as diabetes, Alzheimer's, Parkinson's and Huntington's diseases based on the comparison between known normal levels and abnormal levels of particular substances, e.g. dopamine. The method can be used in combination with and to complement electrophysiologial investigations and spectrophotofluorometric devices for studying calcium and other depolarizing agents in lymphocytes and fibroblasts as well as skin biopsies of patients with diseases, e.g. Alzheimer's and schizophrenia.

Moreover, certain biogenic chemicals measurable by the method of this invention are produced and/or altered in reaction to central or peripheral administration of chemical stimuli, such as drugs. These chemicals which may produce such reactions are psychopharmacological and neuropsychopharmacological agents such as neuroleptics, neuropeptides, amino acids, analgesics, endorphins, gut and brain hormones, calcium blockers, addictive agents, antidepressants, antianxiety agents, anti-panic agents, amphetamines, particularly beta and gamma-endorphins, enkephalins, enkephalinamides such as D-Met$^2$-Pro$^5$-enkephalinamide, cholecystokinin, dynorphin, marijuana, morphine, cocaine and other drugs and agents known to affect the human condition. Non-electroactive moieties and electroactive moieties which are slow to diffuse may be detected by attaching antigens to antibodies, the antigens having electroactive moieties, such as McCreery has done in vitro. However, in vitro applications are difficult to transfer to in vivo situations. For example, the central nervous system effects on the release and re-uptake of various neurotransmitters after peripherally-administered enkephalinamides have been detected, surprisingly, for the first time using the method of this invention.

The method of this invention can, therefore, be used for studying the mechanisms of action in the brain of particular agents. This would aid in the development of new psychotherapeutic agents by the study of structure-activity relationships of administered drugs. Analogs of the studied drugs could be evaluated for their effect on dynamic biogenic chemical levels in order to develop more effective therapeutic agents which have fewer and less severe side effects.

The following examples further illustrate certain embodiments of the method of this invention. Of course, they do not serve to limit the scope of this invention in any way. It should be noted that FIGS. 4, 5, 6, 9 and 10 illustrate representations of cathodic currents generated by using the method of this invention presented in the upright, nonconventional electrochemical notation. They should not be confused with conventional notation used throughout the descriptive examples.

EXAMPLE 1

The electroanalytical technique of linear potential sweep voltammetry (linear scan voltammetry) with a semidifferential output of current, which was modified according to the method of this invention with novel circuitry for the production of a cathodic (reduction) current was used throughout the following examples.

The components of a DCV-5 detector made by Bioanalytical Systems (BAS-DCV5) were modified according to the method of this invention to produce cathodic circuitry for reproducible detection of biogenic characteristics in diseased and healthy states. The modified DCV-5 was connected to a working electrode and a combined reference/auxiliary electrode. The teflon-coated working microelectrode (150–175 microns) was coated with a material consisting of graphite paste and nujol modified with stearate, which allows the measurement of changes in dopamine concentration without interference from ascorbic acid or the dopamine metabolite, 3,4-dihydroxyphenylacetic acid (DOPAC) and the detection of serotonin without interference from uric acid or the metabolite of serotonin, 5-hydroxyindoleacetic acid.

Adult, male, Sprague-Dawley rats were group housed and fed Purina rat food and water daily. Behavioral and biochemical studies were routinely carried out on these rats in the afternoons for better reproducibility. Surgical experiments were carried out in the mornings.

Prior to testing, a reproducible stable baseline measurement of the test rats' dopamine level was achieved in a period of 1.25 hours. The microelectrodes were first tested in vitro in phosphate buffer solution pH 7.4 (0.16M NaCl). Potentials were applied within a range of −0.001 to +0.5 v. The potentials were measured with respect to a reference Ag/AgCl electrode. Both the reference electrode and a platinum auxiliary electrode were placed in contact with the cortex of the brain. A stainless steel auxiliary electrode may also be used. The working electrode was stereotaxically implanted, using a David Kopf stereotoxic device, in the tuberculum olfactorium, according to the atlas of Pellegrino and Cushman, 1967 (coordinates: 2.6 mm anterior to Bregma, 2.5 mm lateral to midline and 9.5 mm below the dura mater, or skull surface).

On each experimental day, the animals were injected intraperitoneally with D-Ala$^2$-D-Pro$^5$- enkephalinamide monoacetate (DAP) dissolved in distilled water (5 mg/kg/ml), along with other animals injected with appropriate vehicle or saline control injections.

Semiderivative voltammograms from rats anesthetized with chloral hydrate (450 mg/kg) were recorded every ten minutes for up to two hours at a scan rate of 10 mv $sec^{-1}$ and a sensitivity of 0.2 nA $sec^{-\frac{1}{2}}cm^{-1}$.

Figure 4:
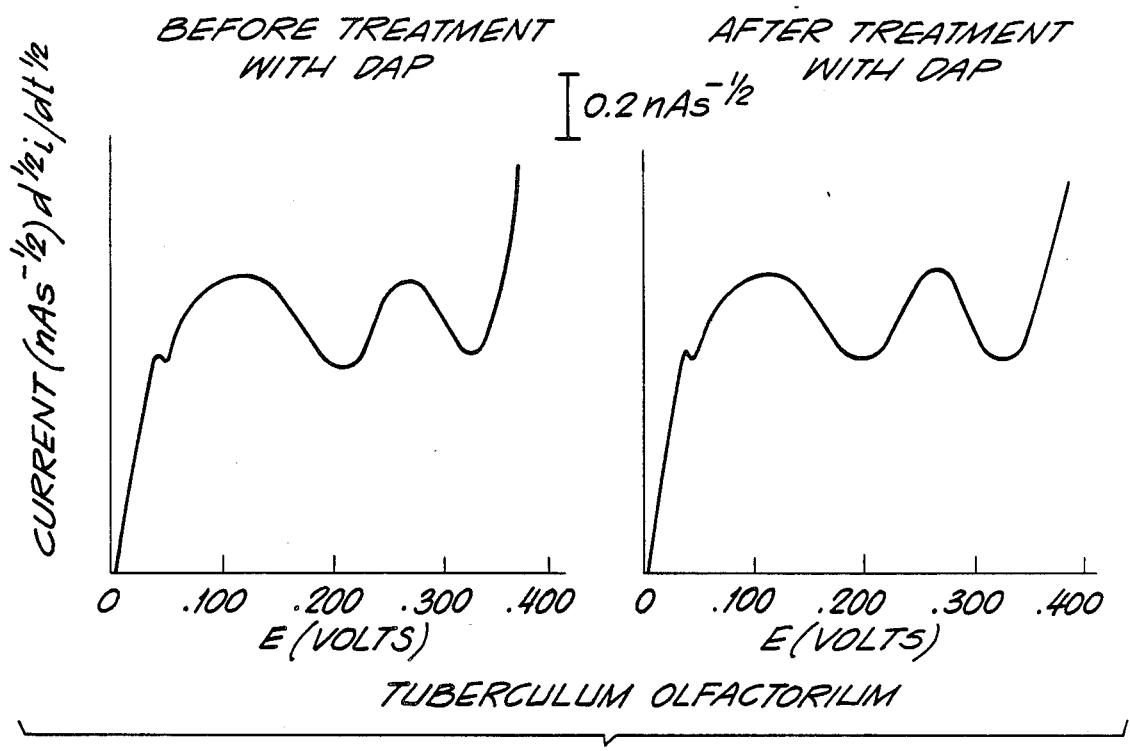
FIG. 4 is a representation of semiderivative voltammograms obtained from the tuberculum olfactorium of the rat brain before and after systemic treatment with D-Ala[2]-D-Pro[5]-enkephalinamide monoacetate (DAP), a compound similar to an endogenous opiate.

Changes in the dopamine signal in the tuberculum olfactorium after injection of DAP enkephalinamide were measured by comparing the mean of the pre-injection values with both the mean and the maximum of the post-injection values. The effects of the administration of the DAP enkephalinamide, in terms of basal dopamine release, is shown in FIG. 4, which shows two semiderivative voltammograms, one pre-injection and one post-injection. The dopamine signal (left-hand peak) is clearly unchanged from pre- to post-injection. The serotonin signal (right-hand peak) is, however, measurably higher after the injection.

It was observed that DAP did not inhibit the rats' locomotor activity. This observation is consistent with conventional theory which places control of locomotor activity in this part of the brain. It shows that dopamine levels in the tuberculum olfactorium are not affected by doses of DAP enkephalinamide. That locomotor activity was not affected is consistent with the placement of locomotor control in the tuberculum olfactorium because behaviorally DAP does not affect locomotor activity.

EXAMPLE 2

Rats were prepared for testing as in Example 1. The rats were injected with d-amphetamine sulfate (2.5 mg/kg) dissolved in saline, or DAP (5 mg/kg) followed in one-half hour by D-amphetamine sulfate. The amphetamine induced stereotypy in the treated rats, i.e. sniffing, head movement, rearing, licking, chewing, grooming, forepaw pacing and locomotor activity were observed. D-Ala$^2$-D-Pro$^5$-enkephalinamide monoacetate was administered intraperitoneally. Changes in central nervous system dopamine concentrations in rat striatum and rat nucleus accumbens (coordinates adjusted to 4.0 mm and 7.5 mm below dura mater), after administering the enkephalinamide were measured by comparing the mean of the pre-injection values with both the mean and the maximum of post-injection values. FIG. 5 shows semiderivative voltammograms from rat striatum (FIG. 5A) and rat nucleus accumbens (FIG. 5B). The semiderivative voltammograms show a significantly decreased signal from the striatum and no change in the signal from the nucleus accumbens. It was observed that the DAP inhibited head-bobbing, sniffing and frequency of rearing. It did not significantly inhibit the amphetamine-induced effect on locomotor activity. This is consistent with behavioral theory that associates stereotyped behaviors with nigrostriatal dopamine activation and locomotor activity with mesolimbic areas of the brain such as nucleus accumbens.

EXAMPLE 3

Rats were prepared for intraperitoneal administration of drug as in Example 1. D-morphine sulfate in distilled water solution was injected intraperitoneally (about 5 mg/kg rat weight) one hour after reproducible basal dopamine and serotonin signals were recorded from rat anterior striatum. The effect of morphine on striatal dopamine and serotonin signals was studied for a period of three hours. Alterations in the dopamine and serotonin signals after morphine was injected were measured by comparing the mean of pre-morphine injection values with both the mean and the maximum of post-morphine injection values. FIG. 6 shows the resultant semiderivative voltammograms taken 1, 2 and 3 hours after administration of morphine and shows changes in release and/or reuptake of brain chemicals in response to the drug. The results can be directly related to brain somatosensory systems involving tolerance to pain, addiction mechanisms and mechanisms of brain reward.

EXAMPLE 4

The method of this invention was used to diagnose diabetes mellitus as follows: male Sprague-Dawley rats were made diabetic with a single intraperitoneal injection of streptozotocin, 60 mg/kg. The diabetic state was assessed by positive glucose concentrations via urine analysis and by measurement of unfasting plasma glucose with the glucose oxidase 2 method (Beckman Glucose Analyzer). Blood was taken from the animals in capillary tubes via the intraocular method. Plasma glucose levels were in excess of 300 mg/100 mL. Neurotransmitters from these animals were studied along with age-matched controls at 3-day-and-a-month intervals following the induction of diabetes by measuring rate of release and reuptake, using the circuit set forth in FIG. 15. The method of this invention was used to measure percent change from endogenously released dopamine and serotonin signals in a non-diabetic rat. The results of these measurements are diagrammed in FIG. 7. The method of this invention can therefore be applied to diagnose diseased states. The results show that serotonin is particularly vulnerable to the diabetic state and may indeed cause endogenous depression.

EXAMPLE 5

The method of Example 4 was used to study the dopamine signals from the brains of rats partially depleted of oxygen such as may be observed in brain injuries. This condition is known as "hypoxic hypoxia".

The left femoral artery of male Wistar rats (260–360 g) was cannulated for measurements of arterial partial pressures of oxygen ($PaO_2$) and carbon dioxide ($PaCO_2$) to determine the degree of hypoxia produced by a 15% $O_2$ inspiratory gas mixture. Bloods were drawn into 150 uL sodium heparin capillary tubes. Blood gases were measured by the ABL 30 Blood Gas Analyzer (Radiometer Amer. Inc., Westlake, Ohio). Gases were administered at a flow rate of six cubic feet per hour via a glove apparatus fitted over the animals' nose and mouth. Compressed air was administered to the animal. After a reproducible and stable baseline of extracellular dopamine and serotonin was evident, the animal was treated with 15% $O_2$ (See FIG. 8). The 15% $O_2$ was followed by compressed air treatment and repeated. The first recording in each treatment group was taken two minutes after the respective treatment was begun.

The administration of 15% $O_2$ treatment produced a significant increase on rat striatal extracellular dopamine whereas administration of 20% $O_2$ returned the dopamine signal to control values. A second 15% $O_2$ treatment caused an irreversible increase in rat striatal extracellular dopamine. Data from femoral artery cannulations showed that $PaO_2$ values decreased as expected during the administration of 15% $O_2$ and returned to normoxic levels during the administration of each 20% $O_2$ treatment. Administration of 15% $O_2$ produced no significant effects on rat striatal extracellular serotonin.

EXAMPLE 6

The method of Example 4 was used to study pain or "analgetic" mechanisms. These mechanisms reflect cerebral blood flow related abnormalities related to somatosensory function and mechanisms of brain reward and drug addiction. These studies of brain analgetic mechanisms, use the opioid peptide, dynorphin. Dynorphin is a non-addicting opioid. FIG. 9a shows a typical voltammogram, of dopamine and serotonin release from rat striatum. Dopamine peaks at +130–+150 mv and serotonin peaks at +270–+290 mv when stearate is added to the graphite in vivo microelectrode. The effect of dynorphin administration on rat striatal dopamine and serotonin release is shown in FIG. 9b. Dopamine release decreased significantly, (30% below control value) and serotonin release increased significantly (40% above control values). The opposing effects of dynorphin occurred over a three-hour period after the administration of dynorphin. These results show that dynorphin does interact with analgetic brain mechanisms.

EXAMPLE 7

The effect of cocaine on dopamine release from striata of male, Sprague-Dawley rats was studied using the method of Example 4. The rats were injected with 20 mg/kg of cocaine subcutaneously. Chloral hydrate anesthetized rats underwent stereotaxic surgery for positioning in the anterior striatum of a teflon-coated working graphite electrode modified by stearate. A Ag/AgCl reference electrode and a stainless steel auxiliary electrode were placed in contact with the rat cortex. Semiderivative voltammograms were recorded every ten minutes. Potentials were applied between −200 and +500 mv, at a scan rate of 10 mv/sec. The results of these scans are illustrated in FIG. 10A as the percentage of basal dopamine release over a period of time, i.e. a decreased dopamine release was observed, emphasizing the control of dopaminergic function across membranes in brain reward and addiction processes.

A rat died of respiratory arrest after being administered a cocaine dose and was subsequently measured for dopamine release. The results of this measurement were compared to a similar measurement in a rat which had not received cocaine. These measurements are set forth in FIGS. 10(b) showing that cocaine has a direct effect on the membrane.

Additional examples of the results of the use of the method and apparatus of this invention are set forth in Patricia A. Broderick, "Rat Striatal Dopamine Release Mechanisms of Cocaine" National Institute Drug Abuse Research Monographs, 1986; Patricia A. Broderick, "Delineation of Striatal Dopaminergic Autoreceptor Agonist Properties of -(-) Apomorphine with In Vivo Electrochemistry", Annals of the New York Acad. Sc., 1985 Vol. No. 473, 1986; Patricia A. Broderick, "In Vivo Electrochemical Studies of Rat Striatal Dopamine and Serotonin Release After Morphine," Life Sciences, Vol. 36, p. 2269, 1985. Patricia A. Broderick, "Opiate Regulation of Mesolimbic Serotonin Release . . . ", Neuropeptides Vol. 5, p. 587, 1985; Patricia A. Broderick et al. "Decreased Release of Striatal Serotonin and Dopamine in the Diabetic Rat As Measured By In Vivo Voltammetry;" The Endocrine Society, 1985; Patricia A. Broderick, et al., "In Vivo Electrochemical and Behavioral Evidence for Specific Neural Substrates Modulated Differentially by Enkephalin in Rat Stimulant Stereotypy and Locomotion;" Biological Psychiatry, Vol. 19, No. 1, p. 45, 1984; Patricia A. Broderick, et al., "Similar Effects of an Enkephalin Analog on Mesolimbic Dopamine Release and Hyperactivity in Rats;" Life Sci. Vol. 33, p. 635, 1983; Patricia A. Broderick et al., "In Vivo Electrochemical Evidence for an Enkephalinergic Modulation Underlying Stereotyped Behaviour: Reversibility By Naloxone;" Brain Res. Vol. 269, p. 378. 1983.

What is claimed is:

1. A method for measuring the rate of release and/or reuptake of one or more biogenic chemicals in vivo and in situ in a warm-blooded or cold-blooded animal brain or body comprising:
    connecting said brain or body to an electrical circuit comprising:
        an auxiliary electrode placed in contact with an outer layer of an organ or sub-organ to be analyzed;
        a reference electrode placed in contact with said outer layer of said organ or sub-organ to be analyzed;
        an indicator microelectrode which is packed with graphite paste and mineral oil modified with a compound selected from the group of fatty acids, fatty acid derivatives, perfluorosulfonated compounds and salts thereof which is inserted into said organ or sub-organ's interior;
        a D.C. source and means for forming cathodic current connected between said reference electrode and said indicator electrode; said organ or sub-organ, auxiliary electrode, reference electrode and indicator electrode thus forming an electrochemical cell which produces output cathodic current;
    means connected in series with said reference electrode for semidifferentiating the cathodic current and;
    processing the signal which represents the output current as the semiderivative of the linear current function;
    thereby producing a cathodic current which represents the rates of release and/or reuptake of one or more biogenic chemicals, the cathodic current enabling the detection of one or more biogenic chemicals which are reduced as well as oxidized and which therefore provides for reproducible results.

2. A method according to claim 1 wherein said biogenic chemicals are selected from the group consisting of amines, amine metabolites, ascorbic acid, amino acids, and neuropeptides.

3. A method according to claim 1 wherein the presence of said biogenic chemicals are measured in the central nervous system after the peripheral administration of a drug.

4. A method according to claim 1 wherein said biogenic chemicals are measured after the central administration of a drug.

5. A method according to claim 1 wherein said cathodic current is transmitted to a receiver telemetrically.

6. A method according to claim 1 wherein a chemical substance is administered to the animal after a reproducible baseline value is achieved.

7. A method according to claim 6 wherein said chemical substance is a neuropsychopharmacological agent selected from the group consisting of antidepressants, neuroleptics, antianxiety agents, anti-panic agents, antimanic/depressive agents, calcium-blocking agents, agents of addiction, enkephalins, enkephalinamides, endorphins and dynorphin.

8. A method according to claim 7 wherein said indicator microelectrode is a Teflon-coated microelectrode homogeneously packed with graphite paste and mineral oil.

9. A method according to claim 8 wherein said modifying compound is selected from the group consisting of acylglycerols, phosphoglycerides, sphingolipids and waxes.

10. A method according to claim 8 wherein said modifying compound is arachadic acid.

11. A method for diagnosing mental illness comprising measuring levels of biogenic chemicals according to the method of claim 1 and comparing said levels to the levels of said chemicals from healthy individuals.

12. A method of elucidating behavioral determinants by measuring levels of biogenic chemicals using the method according to claim 1 and correlating said levels with physiological attributes.

13. A method according to claim 1 comprising measuring the rates of release and reuptake of at least two biogenic chemicals having approximately identical oxidation potentials and different reduction potentials.

14. A method according to claim 1 for diagnosing and studying brain reward/brain pain systems, euphoria, drug addiction, alcohol dependency, diabetes, self-administration of drugs, stereotypy, catalepsy, antianxiety or anxiety paradigms, turning behavior paradigms, reactions to environmental stimuli, conflict/avoidance paradigms, muricide, memory loss, brain injury, and cervical cancer.

15. A method according to claim 1, wherein semiderivative voltammetry is employed for detecting the production of one or more biogenic chemical peaks which represent neurotransmitter and neurotransmitter-like peptides.

16. A method to claim 15 wherein the biogenic chemical peaks produced are at 150, 290, 520, 690, 790, 820 and 910 mv on a semidifferential voltammogram.

17. A method according to claim 1 for detecting non-electroactive moieties and electroactive moieties which are slow to diffuse, in vivo by attaching antigens to antibodies, the antigen having electroactive moieties.

18. A method according to claim 1 wherein neurochemical profiles from different brain regions are provided.

19. A method according to claim 18 wherein the neurochemical profiles are employed for neurochemical mapping for diagnosis of disease.

20. An electrical circuit capable of analyzing the concentration of one or more biogenic chemicals in vivo comprising:
an auxiliary electrode for placing in contact with an outer layer of an organ or sub-organ to be analyzed;
a reference electrode for placing in contact with said outer layer of said organ or sub-organ to be analyzed;
an indicator microelectrode which is packed with graphite paste and mineral oil modified with a compound selected from the group of fatty acids, fatty acid derivatives, perfluorosulfonated compounds and salts thereof, for inserting into said organ or sub-organ's interior;

a D.C. source and means for forming cathodic current connected between said reference electrode and said indicator electrode; whereby said organ or sub-organ, auxiliary electrode, reference electrode and indicator electrode form an electrochemical cell which produces output cathodic current; and means connected in series with said reference electrode for semidifferentiating the cathodic current.

21. The circuit of claim 20 wherein said means for semidifferentiating the cathodic current comprises a differential operational amplifier including a ladder network of resistors and capacitors.

22. The circuit of claim 21 wherein said means for controlling comprises an operational amplifier.

23. The circuit of claim 22 wherein the circuit further comprises a reduction amplifier connected in series with said means for semidifferentiating.

24. The circuit of claim 23 wherein said means for receiving said telemetrically transmitted signals comprises a dual antenna network comprising two parallel branches, each branch comprising in series one or more radio frequency amplification stages, a mixer stage, one or more intermediate frequency stages, and a local oscillator connected to both mixer stages to provide uniformity in the intermediate frequency.

25. The circuit of claim 24 further comprising means connected to outputs of said dual antenna network for providing an analog current signal, and means for visually displaying said signal.

26. The circuit of claim 20 further comprising a reduction current amplifier connected in series to the output of said means for semidifferentiating the cathodic current, said reduction current amplifier having output terminals on which measurements can be made which are indicative of the instantaneous rate mechanism of said biogenic chemicals in an organism.

27. The circuit of claim 26 further comprising a current measuring operational amplifier connected between said indicator electrode and ground.

28. The circuit of claim 27 further comprising an operational amplifier connected between said indicator electrode and said auxiliary electrode, and another operational amplifier connected between said indicator electrode and said reduction current amplifier whereby an output which produces a linear trace on an analog recorder may be obtained from said reduction current amplifier.

29. The circuit of claim 20 further comprising means for controlling the electrical potential of said auxiliary electrode, said means for controlling being connected to said auxiliary electrode and to ground.

30. The circuit of claim 29 further comprising a follower operational amplifier connected between said reference electrode and ground.

31. The circuit of claim 20 further comprising means for telemetrically transmitting signals proportional to said cathodic current and means for receiving said transmitted signals.

32. The circuit of claim 20 wherein said means for differentiating the cathode current comprises a differential amplifier.

33. The circuit of claim 20 further comprising means for automatically operating said circuit.

34. The circuit of claim 33 wherein said automatically operated means comprises a transistor-transistor logic connected to said means for initiating scans and regulating the voltage level of said scans.

* * * * *

UNITED STATES PATENT AND TRADEMARK OFFICE
CERTIFICATE OF CORRECTION

PATENT NO. : 4,883,057
DATED : November 28, 1989
INVENTOR(S) : Dr. Patricia A. Broderick It is certified that error appears in the above-identified patent and that said Letters Patent is hereby corrected as shown below:

Column 1, line 26, after "types" insert -- of biogenic --.

Column 11, line 62, change "stereotype" to -- stereotypy --.

Column 15, line 54, delete "V = -1/c";
line 57, delete " $\int idt = -\frac{1}{CR} \int Vidt$" and insert
-- $V_o = -\frac{1}{C} \int idt = -\frac{1}{CR} \int Vidt$ --.

Column 10, line 64, change "arachadic" to -- arachidic --.

Claim 10, line 2, change "arachadic" to -- arachidic --.

Signed and Sealed this

Twenty-ninth Day of June, 1993

Attest:

MICHAEL K. KIRK

*Attesting Officer*   *Acting Commissioner of Patents and Trademarks*